US009782152B2

(12) United States Patent
Miga et al.

(10) Patent No.: US 9,782,152 B2
(45) Date of Patent: Oct. 10, 2017

(54) METHOD AND SYSTEM FOR REAL-TIME COMPRESSION CORRECTION FOR TRACKED ULTRASOUND AND APPLICATIONS OF SAME

(71) Applicant: Vanderbilt University, Nashville, TN (US)

(72) Inventors: Michael I. Miga, Franklin, TN (US); Thomas S. Pheiffer, Langhorne, PA (US)

(73) Assignee: VANDERBILT UNIVERSITY, Nashville, TN (US)

( * ) Notice: Subject to any disclaimer, the term of this patent is extended or adjusted under 35 U.S.C. 154(b) by 192 days.

(21) Appl. No.: 14/829,494

(22) Filed: Aug. 18, 2015

(65) Prior Publication Data

US 2016/0048958 A1 Feb. 18, 2016

Related U.S. Application Data

(60) Provisional application No. 62/038,652, filed on Aug. 18, 2014, provisional application No. 62/130,329, filed on Mar. 9, 2015.

(51) Int. Cl.
*A61B 8/08* (2006.01)
*A61B 8/00* (2006.01)
(Continued)

(52) U.S. Cl.
CPC .............. *A61B 8/58* (2013.01); *A61B 8/4254* (2013.01); *A61B 8/466* (2013.01); *A61B 8/483* (2013.01);
(Continued)

(58) Field of Classification Search
CPC ..... A61B 6/032; A61B 6/5247; A61B 8/4254; A61B 8/466; A61B 8/483; A61B 8/485;
(Continued)

(56) References Cited

U.S. PATENT DOCUMENTS

| 9,607,405 B2* | 3/2017 | Li .............................. G06T 7/60 |
| 2004/0009459 A1* | 1/2004 | Anderson ........... G06F 19/3406 434/262 |

(Continued)

OTHER PUBLICATIONS

Cash et al., "Compensating for Intraoperative Soft-Tissue Deformations Using Incomplete Surface Data and Finite Elements", 2005, IEEE Transactions on Medical Imaging, vol. 24, No. 11, 1479-1491.*

(Continued)

*Primary Examiner* — Katrina Fujita
(74) *Attorney, Agent, or Firm* — Locke Lord LLP; Tim Tingkang Xia, Esq.

(57) ABSTRACT

A method for real-time correction of tissue compression for tracked ultrasound includes acquiring an ultrasound image of tissues of interest with an ultrasound probe having a probe surface, where the ultrasound probe is tracked to provide a position and an orientation of the probe surface of the ultrasound probe for the acquired ultrasound image; acquiring intraoperative measurements of the undeformed tissue surface; constructing a generic grid representation of tissues for use with a mathematical model of tissue biomechanics, where the generic grid representation is pre-aligned to the acquired ultrasound image by performing a calibration to the ultrasound probe; determining boundary conditions to the mathematical model represented by the generic grid representation; solving the mathematical model for 3D displacements in the generic grid representation of the tissues; and performing correction of tissue compression by using the reversed and interpolated 3D displacement field on the acquired ultrasound image.

29 Claims, 12 Drawing Sheets

(51) Int. Cl.
G06F 17/50 (2006.01)
A61B 6/03 (2006.01)
A61B 6/00 (2006.01)
A61B 90/00 (2016.01)

(52) U.S. Cl.
CPC ............ *A61B 8/485* (2013.01); *A61B 8/5207* (2013.01); *A61B 8/5261* (2013.01); *A61B 8/5269* (2013.01); *A61B 8/587* (2013.01); *G06F 17/50* (2013.01); *A61B 6/032* (2013.01); *A61B 6/5247* (2013.01); *A61B 2090/378* (2016.02)

(58) Field of Classification Search
CPC ... A61B 8/5207; A61B 8/5261; A61B 8/5269; A61B 8/58; A61B 8/587; A61B 2090/378; G06F 17/50
See application file for complete search history.

(56) References Cited

U.S. PATENT DOCUMENTS

| | | | |
|---|---|---|---|
| 2005/0101855 A1* | 5/2005 | Miga | G06T 7/38 600/407 |
| 2009/0216119 A1* | 8/2009 | Fan | A61B 5/0048 600/438 |
| 2010/0016724 A1* | 1/2010 | Arai | A61B 8/08 600/443 |
| 2010/0160778 A1* | 6/2010 | Eskandari | A61B 8/00 600/438 |
| 2011/0216958 A1* | 9/2011 | Satoh | A61B 8/5261 382/131 |
| 2012/0232386 A1* | 9/2012 | Mansi | A61B 8/0883 600/437 |
| 2014/0037161 A1* | 2/2014 | Rucker | G06T 7/30 382/128 |
| 2014/0133727 A1* | 5/2014 | Oktay | G06T 7/33 382/131 |
| 2014/0254869 A1* | 9/2014 | Li | G01N 29/0654 382/103 |
| 2015/0216496 A1* | 8/2015 | Lee | G06T 7/0012 600/425 |

OTHER PUBLICATIONS

Pheiffer et al., "Automatic Generation of Boundary Conditions Using Demons Nonrigid Image Registration for Use in 3-D Modality-Independent Elastography", 2011, IEEE Transactions on Biomedical Engineering, vol. 58, No. 9, 2607-2616.*
Pheiffer et al., "Geometric reconstruction using tracked ultrasound strain imaging", Mar. 2013, Proc. SPIE 8671, Medical Imaging 2013: Image-Guided Procedures, Robotic Interventions, and Modeling, 86711E.*
Rizzo, Frank J. "An integral equation approach to boundary value problems of classical elastostatics." Quarterly of Applied Mathematics 25.1 (1967): 83-95.*
Simpson et al., "Comparison Study of Intraoperative Surface Acquisition Methods for Surgical Navigation", Apr. 2013, IEEE Transactions on Biomedical Engineering, vol. 60, No. 4, 1090-1099.*
Wang et al., "Boundary conditions in photoacoustic tomography and image reconstruction", 2007, J. Biomed. Opt. 12(1), 014027.*
Treece GM, Gee AH, Prager RW (2005) RF and amplitude-based probe pressure correction for 3D ultrasound. Ultrasound Med Biol 31 (4):493-503. doi:S0301-5629(04)00441-7 [pii] 10.1016/j.ultrasmedbio.2004.12.018.
Kiao G, Brady JM, Noble JA, Burcher M, English R (2002) Nonrigid registration of 3-D free-hand ultrasound images of the breast. IEEE Trans Med Imaging 21 (4):405-412. doi:10.1109/TMI.2002.1000264.
Burcher MR, Lianghao H, Noble JA Deformation correction in ultrasound images using contact force measurements. In: Mathematical Methods in Biomedical Image Analysis, 2001. MMBIA 2001. IEEE Workshop on, 2001 2001. pp. 53-70. doi:10.1109/mmbia.2001.991700.
Sun S-Y (2010) Deformation correction in ultrasound imaging in an elastography framework. Thesis S.M.—Massachusetts Institute of Technology Dept. of Electrical Engineering and Computer Science 2010., Massachusetts Institute of Technology, Cambridge.
Pheiffer TS, Thompson RC, Rucker DC, Simpson AL, Miga MI (2014) Model-Based Correction of Tissue Compression or Tracked Ultrasound in Soft Tissue Image-Guided Surgery. Ultrasound Med Biol. doi:S0301-5629(13)01146-0 [pii] 10.1016/j.ultrasmedbio.2013.11.003.
Rucker DC, Wu Y, Clements LW, Ondrake JE, Pheiffer TS, Simpson AL, Jamagin WR, Miga MI (2013) A Mechanics-Based Nonrigid Registration Method for Liver Surgery Using Sparse Intraoperative Data. Medical Imaging, IEEE Transactions on 33 (1):147-158. doi:10.1109/tmi.2013.2283016.
Lange T, Papenberg N, Heldmann S, Modersitzki J, Fischer B, Lamecker H, Schlag PM (2009) 3D ultrasound-CT registration of the liver using combined landmark-intensity information. International Journal of Computer Assisted Radiology and Surgery 4 (1):79-88. doi:Doi 10.10071s11548-008-0270-1.
Chen I, Ong RE, Simpson AL, Sun K, Thompson RC, Miga MI (2013) Integrating Retraction Modeling Into an Atlas-Based Framework for Brain Shift Prediction. Ieee Transactions on Biomedical Engineering 60 (12):3494-3504. doi:Doi10.1109/Tbme.2013.2272658.
Coffey AM, Miga MI, Chen I, Thompson RC (2013) Toward a preoperative planning tool for brain tumor resection therapies. International Journal of Computer Assisted Radiology and Surgery 8 (1):87-97. doi:DOI 10.1007/s11548-012-0693-6.
Bro-Nielsen M (1998) Finite element modeling in surgery simulation. Proceedings of the IEEE 86 (3):490-503. doi:Doi 10.1109/5.662874.
Sullivan JM, Charron G, Paulsen KD (1997) A three-dimensional mesh generator for arbitrary multiple material domains. Finite Elements in Analysis and Design 25 (3-4):219-241. doi:Doi 10.1016/S0168-874x(96)00027-3.
Arun KS, Huang TS, Blostein SD (1987) Least-Squares Fitting of 2 3-D Point Sets. Ieee Transactions on Pattern Analysis and Machine Intelligence 9 (5):699-700.
Besl PJ, Mckay ND (1992) A Method for Registration of 3-D Shapes. Ieee Transactions on Pattern Analysis and Machine Intelligence 14 (2):239-256.
Muratore DM, Galloway RL (2001) Beam calibration without a phantom for creating a 3-D freehand ultrasound system. Ultrasound in Medicine and Biology 27 (11):1557-1566.
Pheiffer TS, Simpson AL, Lennon B, Thompson RC, Miga MI (2012) Design and evaluation of an optically-tracked single-CCD laser range scanner. Med Phys 39 (2):636-642. doi:10.1118/1.3675397.
Dubuisson MP, Jain AK A modified Hausdorff distance for object matching. In: Pattern Recognition, 1994. vol. 1—Conference A: Computer Vision Image Processing., Proceedings of the 12th IAPR International Conference on, Oct. 9-13, 1994 1994. pp. 566-568 vol. 561. doi:10.1109/icpr.1994.576361.
Dumpuri P, Thompson RC, Dawant BM, Cao A, Miga MI (2007) An atlas-based method to compensate for brain shift: preliminary results. Med Image Anal 11 (2):128-145. doi:51361-8415(06)00081-8 [pii] 10.1016/j.media.2006.11.002.
Miller KE, Ondrake JE, Pheiffer TS, Simpson AL, Miga MI Utilizing ultrasound as a surface digitization tool in image guided liver surgery. In: David RH, III, Kenneth HW (eds), 2012. SPIE, p. 83163D.
Kumar AN, Miga MI, Pheiffer TS, Chambless LB, Thompson RC, Dawant BM (2015) Persistent and automatic intraoperative 3D digitization of surfaces under dynamic magnifications of an operating microscope. Medical Image Analysis 19 (1):30-45. doi:DOI 10.1016/j.media.2014.07.004.
Lange T, Eulenstein S, Hunerbein M, Lamecker H, Schlag PM (2004) Augmenting intraoperative 3D ultrasound with preoperative

(56) References Cited

OTHER PUBLICATIONS models for navigation in liver surgery. Medical Image Computing and Computer-Assisted Intervention—Miccai 2004, Pt 2, Proceedings 3217:534-541.

* cited by examiner

METHOD AND SYSTEM FOR REAL-TIME COMPRESSION CORRECTION FOR TRACKED ULTRASOUND AND APPLICATIONS OF SAME

CROSS-REFERENCE TO RELATED PATENT APPLICATIONS

This application claims priority to and the benefit of, pursuant to 35 U.S.C. §119(e), U.S. Provisional Patent Application Ser. Nos. 62/038,652, filed Aug. 18, 2014, and 62/130,329, filed Mar. 9, 2015, both entitled "MODEL-BASED COMPRESSION CORRECTION FRAMEWORK FOR ULTRASOUND", by Michael I. Miga and Thomas S. Pheiffer, which are incorporated herein in their entireties by reference.

Some references, which may include patents, patent applications and various publications, are cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [5] represents the 5th reference cited in the reference list, namely, Pheiffer T S, Thompson R C, Rucker D C, Simpson A L, Miga M I (2014) Model-Based Correction of Tissue Compression for Tracked Ultrasound in Soft Tissue Image-Guided Surgery. Ultrasound Med Biol. doi:S0301-5629(13)01146-0 [pii] 10.1016/j.ultrasmedbio.2013.11.003.

STATEMENT AS TO RIGHTS UNDER FEDERALLY-SPONSORED RESEARCH

This invention was made with government support under grant numbers R01NS049251 and R01CA162477, awarded by the National Institutes of Health. The government has certain rights in the invention.

FIELD OF THE INVENTION

The invention relates generally to ultrasound imaging, and more particularly, to methods and systems that utilize a generic mathematical model of tissues for real-time correction of tissue compression exerted by an ultrasound probe and applications of the same.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the present invention.

Ultrasound is ubiquitous as an interventional and diagnostic imaging modality, and is commonly used to assess the location and geometry of disease intraoperatively. An inherent problem with this role is the shape distortion of visualized tissue structures introduced by the probe pressure exerted. It is widely recognized that relatively large tissue compression can occur in soft tissue anatomy, e.g. the liver or breast. As a result, compression can obfuscate geometrical and locational measurements of subsurface targets such as tumors. This is particularly a problem for image-guided interventions which rely upon tracked ultrasound to provide intraoperative spatial measurements of structures taken during an intervention and then compared to their co-registered preoperative imaging data counterparts. Nonrigid tissue compression is a primary cause of misalignment and shape distortion with these other sources of information. As image-guided navigation strategies in soft tissue environments continue to be developed, methods of correcting the tissue deformation from routine ultrasound imaging are necessary in order to ensure that all of these data are in a consistent spatial arrangement.

There are several methods described in the literature for performing compression correction. A common approach is to utilize the intensity information in the ultrasound images to perform a nonrigid intensity-based registration with positional tracking of compressed images over a range of compression states [1, 2]. One drawback of this method is that it requires a stream of ultrasound images, and intensity based registration for ultrasound is a challenging task in practice. For example, Treece et al. [1] demonstrated a method to correct for compression using correlation of a stream of radiofrequency (RF) or amplitude frames, and although the method performed well in a phantom dataset, the authors noted its reliance on good image quality as well as the possibility of correction drift when compression estimates are accumulated across a large sequence of images. Another method of correction is to use a mechanical model of the tissue in order to estimate the subsurface tissue displacements caused by the interaction of the probe with the tissue surface. One group proposed using a force measurement apparatus to provide force boundary conditions to a tissue model [3, 4], although force boundary conditions require some prior estimate of absolute material properties for the tissue. An alternative method has recently been proposed, which utilizes a biomechanical model based correction which is driven by displacement boundary conditions provided by the position of a tracked ultrasound probe within a co-registered patient-specific organ surface from preoperative tomograms [5]. This method was shown to reduce ultrasound compressional error of nearly 1 cm to approximately 2 to 3 mm.

There is a subset of image-guided procedures for which preoperative tomographic image volumes are not commonly acquired, or the volumes are acquired with the patient in a much different presentation than the operative state. This can be the case in open liver surgery, for example, in which there is often significant manipulation of the organ by the surgeon leading up to the surgical presentation of the tissue. Therefore, a method of compression compensation that does not rely on a preoperative model would be more valuable. In addition, it is often the case that subsurface structures may be necessary for enhancing image-to-physical registration, and it is easily seen that there are implications if subsurface deformation is not addressed in registration frameworks.

Provided with at least some form of intraoperative measurement of compression, subsurface structures could be uncompressed to give true shapes in physical space. These true subsurface shapes could then be used in combination with surface information to compute a combined image-to-physical registration. An example of this would be a registration framework that used a surface point cloud from a laser measurement device and subsurface structures like a tumor [6] or perhaps blood vessels [7]. This is just one embodiment of how true-shape subsurface tissue structures as described by an uncompressed ultrasound imaging technique could be used.

Therefore, a heretofore unaddressed need exists in the art to address the aforementioned deficiencies and inadequacies.

SUMMARY OF THE INVENTION

One of the objectives of the invention is to provide a real-time compression correction method to correct tissue compression for tracked ultrasound. In one aspect of the invention, the method utilizes a generic approach that is independent of tomographic imaging and requires no registration to a preoperative surface. In another aspect of the invention, the method utilizes a patient-specific model that requires registration to a preoperative surface. The generic approach is used to produce ultrasound images in which the tissue structures can be rendered in their uncompressed biomechanical state so as to provide more accurate shape measurements or as a source of intraoperative data for geometric comparisons. The compression correction method is compared with the method using a patient-specific model [5] by deployment in phantoms and clinical data.

In certain embodiments, the generic compression correction method models a generic block model of tissue and its subsurface tissue displacements resulting from application of a probe to the tissue surface. According to the invention, the generic compression correction method can be realized independent of preoperative imaging data and is capable of near video frame rate compression compensation for real-time guidance.

In certain embodiments, the block model is calibrated to the tip of any tracked ultrasound probe. Intraoperatively, digitization of the tissue surface is used to measure the depth of compression and provide boundary conditions to the biomechanical model of the tissue. The tissue displacement field solution as calculated by the mathematical model can be used in an inverse manner to non-rigidly transform the ultrasound images to an estimation of the tissue geometry prior to compression. The generic compression correction method was compared to the method using a patient-specific model and within the context of simulation, phantom, and clinical data.

In certain embodiments, tracking and digitization information is utilized to detect the pose of an ultrasound probe within soft tissue during imaging, and to correct the compressional effects in the ultrasound data by using a biomechanical model of the tissue.

In certain embodiments, the compression correction method further requires the surface information be registered to the preoperative data.

In one aspect, the invention relates to a method for real-time correction of tissue compression for tracked ultrasound. In one embodiment, the method includes the following steps: an ultrasound image of tissues of interest is acquired with an ultrasound probe having a probe surface, wherein the ultrasound probe is tracked to provide a position and an orientation of the probe surface of the ultrasound probe for the acquired ultrasound image. In one embodiment, a mathematical representation of soft tissues in contact with the ultrasound probe surface is represented as a block mesh associated with the ultrasound transducer.

Intraoperative measurements of the undeformed tissue surface are acquired; intraoperative measurements of the ultrasound probe and consequently ultrasound probe surface are acquired.

A generic grid representation of tissues is constructed for use with a mathematical model of tissue biomechanics, wherein the generic grid representation is pre-aligned to the acquired ultrasound image by performing a calibration to the ultrasound probe.

Boundary conditions to be applied to the mathematical model are determined by analyzing the difference between the undeformed tissue surface and location of ultrasound probe surface in relation to that undeformed state as provided by tracking technology.

The mathematical representation of the soft tissue as represented by the generic block is solved for three-dimensional (3D) displacements in the block mesh of the tissues; and the displacement field is reversed and interpolated such that the 3D displacements can be applied to the acquired ultrasound image to perform the correction of tissue compression.

In one embodiment, the step of acquiring the ultrasound image further comprises calibrating the ultrasound image to a tracked target that is attached to the ultrasound probe, wherein the ultrasound probe is tracked intraoperatively with a tracking device, so that the pose of the ultrasound image is defined in the coordinate system of the tracking device.

In one embodiment, the pose of the generic grid representation is defined by the same tracking information which defines the pose of the ultrasound image, wherein the tracking information is an optically tracked attached target or electromagnetically attached tracked target.

In one embodiment, the step of acquiring the intraoperative measurements of the undeformed tissue surface is performed with a surface acquiring device that is tracked intraoperatively with the tracking device or contains a geometric reference within the field of view of the surface acquiring device. In one embodiment, the surface acquiring device comprises a laser range scanner (LRS) or a stereo pair camera set.

In one embodiment, the step of acquiring the intraoperative measurements of the undeformed tissue surface is performed with a LRS that is tracked intraoperatively with the tracking device or involves a known geometric reference contained within the field of view of the LRS.

In one embodiment, the LRS is used to construct a digital representation of the probe surface.

In one embodiment, the step of acquiring the intraoperative measurements of the undeformed tissue surface is performed with a stereo pair analysis using computer vision techniques of the tissue surface that is tracked intraoperatively with a tracking device or involves a known geometric reference contained with the field of view of the stereo pair.

In one embodiment, the stereo pair with computer vision techniques is used to construct a digital representation of the probe surface.

In one embodiment, the step of determining the boundary conditions comprises using the undeformed tissue surface in conjunction with the position and orientation of the ultrasound probe to estimate a depth to which the tissues are compressed, wherein the depth is computed by casting rays down from each point of the acquired surface cloud in the depth direction, and finding an average length of the ray segments which intersect with the probe surface.

In another embodiment, the step of determining the boundary conditions comprises using the location of the ultrasound probe as defined by tissue contact determined by detection within the ultrasound image in conjunction with the final position and orientation of the ultrasound probe at the time of subsurface tissue structure visualization to estimate a depth to which the tissues are compressed, wherein the depth is computed by estimating compression depth as determined by analyzing the difference in the probe location between the initial tissue contact and the final structure visualization.

In one embodiment, the depth is used to assign Dirichlet boundary conditions to the mathematical model as represented within a block mesh.

In one embodiment, the boundary conditions for the mathematical model associated with the generic grid representation are assigned such that the far-field face of the generic grid representation is fixed, and the superior and side surfaces are stress-free.

In one embodiment, the mathematical model associated with the generic grid representation calibration is performed by aligning the top of the ultrasound image with the center of one side of the generic grid representation, and aligning the image plane itself with the plane through the center of the generic grid representation.

In one embodiment, the generic grid representation is represented by a mesh comprising nodes in the form of a generic block.

In one embodiment, the biomechanical model is governed by a standard 3D Navier-Cauchy equation for the 3D displacements.

In one embodiment the displacement vector at each node in the block mesh satisfy with:

$$[K]\{u\}=\{f\}$$

where K is the global stiffness matrix, u is the vector of nodal displacements, and f contains the contributions of boundary conditions In one embodiment, the boundary conditions assigned to each boundary node remains the same, such that a stiffness matrix K is pre-computable and reusable for each correction, wherein a vector of nodal displacements u satisfies with:

$$\{u\}=[K]^{-1}\{f\}$$

where f contains contributions of the boundary conditions.

In one embodiment, the method further comprises arranging the order of the mesh node indices to ensure that first N equations belong to the nodes lying on the ultrasound plane, and any nodes on the top surface which are assigned varying amounts of compression boundary conditions, wherein the equation of the displacement vector is expressed as a block matrix system where the subscripts p and a indicate the plane nodes and all other nodes, respectively:

$$\begin{bmatrix} K_{pp} & K_{pa} \\ K_{ap} & K_{aa} \end{bmatrix} \begin{Bmatrix} u_p \\ u_a \end{Bmatrix} = \begin{Bmatrix} f_p \\ f_a \end{Bmatrix}.$$

In one embodiment, the block matrix system is rearranged to a form involving only the displacement solution of the plane nodes, $u_p$:

$$[\check{K}_{pp}]\{u_p\}=\{\check{f}_s\}$$

where $$[\check{K}_{pp}]=[K_{aa}]-[K_{pa}][K_{aa}]^{-1}[K_{ap}]$$

$$\{\check{f}_s\}=\{f_s\}-[K_{pa}][K_{aa}]^{-1}\{f_a\}$$

wherein the modified stiffness matrix $[\check{K}_{pp}]$ represents a transfer of the displacements from all non-plane nodes to the plane nodes, and maintains the volumetric nature of the model, wherein the modified stiffness matrix $[\check{K}_{pp}]$ is a fraction of the size of the full K matrix, and wherein the $u_p$ vector of plane node displacements is pre-computed and stored in a lookup table.

In one embodiment, all nodes in the $f_a$ vector is assigned either zero stress or zero displacement boundary conditions, wherein changes in the compression depth during ultrasound imaging results in a reassignment of the values in $\check{f}_s$:

$$\{\check{f}_s\}|_{\{f_a\}=0}=\{f_s\}.$$

In one embodiment, subsets designated with respect to planes associated with the aboce solutions represent a sub-volume within an ultrasound imaging volume used with multi-dimensional ultrasound arrays.

In one embodiment, the method further comprises registering the surface information to preoperative imaging for determining the boundary conditions.

In one embodiment, the generic grid representation of tissues is constructed from preoperative imaging and registered to intraoperative space.

In one embodiment, more than one generic grid representation of varying sizes can be predetermined to match the changes in field of view use of the ultrasound probe.

In one embodiment, the generic mathematical model associated with the block mesh can be solved with objects of varying material physical properties within the model spatially.

In one embodiment, predetermined generic models with different spatial arrangements of material properties can be combined in the mathematical sense to account for soft tissue material properties that vary in the anatomy.

According to certain embodiments of the invention, experimental results with gel phantoms demonstrated that the generic method reduced the mock tumor margin Modified Hausdorff Distance (MHD) from about 5.0±1.6 mm to about 2.1±0.7 mm, and reduced mock tumor centroid alignment error from about 7.6±2.6 mm to about 2.6±1.1 mm. The method was applied to a clinical case, and reduced the in vivo tumor margin MHD error from about 5.4±0.1 mm to about 2.9±0.1 mm, and the centroid alignment error from about 7.2±0.2 mm to about 3.8±0.4 mm. Thus, the invented method can effectively improve alignment of ultrasound and tomographic images, and is more efficient compared to a previously reported patient-specific compression correction [5].

In another aspect, the invention relates to a system for real-time correction of tissue compression for tracked ultrasound. In one embodiment, the system includes an ultrasound probe configured to acquire an ultrasound image of tissues of interest; a surface acquiring device configured to perform intraoperative measurements of the undeformed tissue surface; a tracking device configured to track the ultrasound probe and the surface acquiring device; and a controller coupled with the ultrasound probe, the surface acquiring device and the tracking device and configured to construct a generic grid representation of tissues for use with a mathematical model of tissue biomechanics, wherein the generic grid representation is pre-aligned to the acquired ultrasound image by performing a calibration to the ultrasound probe; solve the mathematical model of tissue biomechanics for three-dimensional (3D) displacements in the generic grid representation of the tissues, and perform the correction of tissue compression by using the reversed and interpolated 3D displacement field onto the acquired ultrasound image.

In one embodiment, the surface acquiring device is further configured to construct a digital representation of the probe surface.

In one embodiment, the surface acquiring device comprises an LRS or a stereo pair camera set.

In one embodiment, the ultrasound probe is tracked by the tracking device with a tracked attached target to provide a position and an orientation of the probe surface of the ultrasound probe for the acquired ultrasound image.

In one embodiment, the controller is further configured to calibrate the ultrasound image to the tracked attached target, so that the pose of the ultrasound image is defined in the coordinate system of the tracking device.

In one embodiment, the controller is further configured to determine boundary conditions using the undeformed tissue surface in conjunction with the position and orientation of the ultrasound probe to estimate a depth to which the tissues are compressed, wherein the depth is computed by casting rays down from each point of the acquired surface cloud obtained by the surface acquiring device in the depth direction, and finding an average length of the ray segments which intersect with the probe surface.

In another embodiment, the controller is further configured to determine boundary conditions using the undeformed tissue surface as determined by recording the orientation and position of the ultrasound probe at first contact with the tissue in the ultrasound image in conjunction with the position and orientation of the ultrasound probe when placed to visualize the subsurface target, wherein the difference in these positions is used to estimate a depth to which the tissues are compressed.

In one embodiment, the system further comprises a display for displaying at least the ultrasound image, the generic grid representation of the tissues, and the correction of tissue compression.

In one aspect, the invention relates to a non-transitory computer-readable medium storing instructions which, when executed by one or more processors, cause a controller to perform functions for real-time correction of tissue compression for tracked ultrasound.

In one embodiment, the functions comprises calibrating an ultrasound image acquired with an ultrasound probe to a tracked target attached to the ultrasound probe; acquiring intraoperative measurements of the undeformed tissue surface; constructing a a generic grid representation of tissues for use with a mathematical model of tissue biomechanics, wherein the grid representation is pre-aligning the block mesh to the acquired ultrasound image; determining boundary conditions to the mathematical model of tissue biomechanics represented by the generic grid representation; solving the mathematical model of tissue biomechanics for 3D displacements in the generic grid representation of the tissues; and performing the correction of tissue compression by using the reversed and interpolated 3D displacement field onto the acquired ultrasound image.

In one embodiment, the pose of the ultrasound image is defined in the coordinate system of the tracking device.

In one embodiment, the pose of the generic grid representation is defined by the same tracking information which defines the pose of the ultrasound image, wherein the tracking information is an optically tracked attached target or electromagnetically attached tracked target.

In one embodiment, the functions further comprise constructing a digital representation of the probe surface.

In one embodiment, the function of determining the boundary conditions comprises the function of using the undeformed tissue surface in conjunction with the position and orientation of the ultrasound probe to estimate a depth to which the tissues are compressed, wherein the depth is computed by casting rays down from each point of the LRS cloud in the depth direction, and finding an average length of the ray segments which intersect with the probe surface.

In another embodiment, the function of determining boundary conditions using the undeformed tissue surface as determined by recording the orientation and position of the ultrasound probe at first contact with the tissue in the ultrasound image in conjunction with the position and orientation of the ultrasound probe when placed to visualize the subsurface target, wherein the difference in these positions is used to estimate a depth to which the tissues are compressed.

In one embodiment, the depth is used to assign Dirichlet boundary conditions to the mathematical model on the generic grid representation.

In one embodiment, the boundary conditions for the mathematical model associated with the generic grid representation are assigned such that the far-field face of the generic grid representation is fixed, and the superior and side surfaces are stress-free.

In one embodiment, the biomechanical model is governed by a standard 3D Navier-Cauchy equation for the 3D displacements.

These and other aspects of the present invention will become apparent from the following description of the preferred embodiments, taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. The same reference numbers may be used throughout the drawings to refer to the same or like elements in the embodiments.

DETAILED DESCRIPTION OF THE INVENTION

Figure 1:
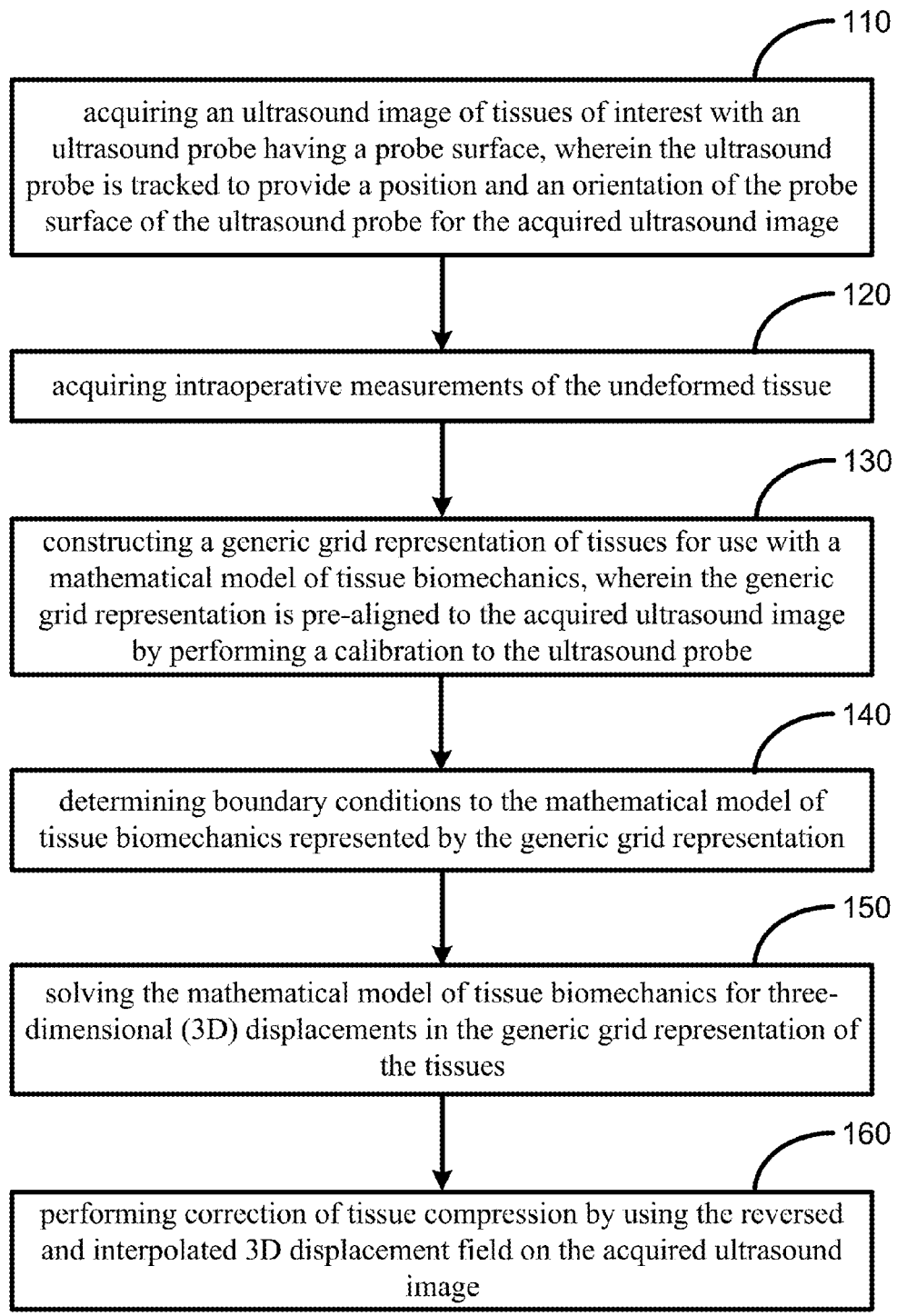
FIG. 1 shows schematically a flowchart for real-time correction of tissue compression for tracked ultrasound according to one embodiment of the invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that, as used in the description herein and throughout the claims that follow, the meaning of "a", "an", and "the" includes plural reference unless the context clearly dictates otherwise. Also, it will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising," or "includes" and/or "including" or "has" and/or "having", or "carry" and/or "carrying," or "contain" and/or "containing," or "involve" and/or "involving, and the like are to be open-ended, i.e., to mean including but not limited to. When used in this invention, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present invention, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the invention.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

The description below is made as to the embodiments of the invention in conjunction with the accompanying drawings. In accordance with the purposes of this invention, as embodied and broadly described herein, this invention, in certain aspects, relates to methods and systems that utilize a generic block model of tissues for real-time correction of tissue compression exerted by an ultrasound probe and applications of the same.

Overview

In one aspect of the invention, the compression correction method models a generic block model of tissue and its subsurface tissue displacements resulting from application of a probe to the tissue surface. According to the invention, the compression correction method can be realized independent of preoperative imaging data and is capable of near video frame rate compression compensation for real-time guidance.

In another aspect, the invention relates to methods that utilize tracking and digitization information to detect the pose of an ultrasound probe within soft tissue during imaging, and use that information to correct the compressional effects in the ultrasound data by using a biomechanical model of the tissue.

Referring to FIG. 1, a flowchart for real-time correction of tissue compression exerted by an ultrasound probe is schematically shown according to one embodiment of the invention. In the exemplary embodiment, an ultrasound image of tissues of interest is acquired with an ultrasound probe at step 110. The ultrasound probe is tracked with tracking device to provide a position and an orientation of the probe surface of the ultrasound probe for the acquired ultrasound image. In one embodiment, the ultrasound image is calibrated to a tracked target attached to the ultrasound probe, so that the pose of the ultrasound image is defined in the coordinate system of the tracking device. In addition, a digital representation of the probe surface can be constructed by a surface acquiring device, such as an LRS, or a stereo pair camera set. For example, the LRS scans the face of the ultrasound probe to create a 3D point cloud representing the probe surface. LRS scan of the probe surface is necessary only in the absence of 3D geometry files from the ultrasound probe manufacturer, which can be used to provide an equivalent geometry.

The LRS is also tracked by the same tracking system as the ultrasound probe during the scan, and thus, the created point cloud has a known pose based on the pose of the probe. As a consequence of this relationship and the tracking of the ultrasound probe during data acquisition, the position and orientation of the digital probe surface are known for every ultrasound image collected.

At step 120, intraoperative measurements of the undeformed tissue surface are acquired.

At step 130, a generic grid representation of tissues for use with a mathematical model of tissue biomechanics is constructed. The generic grid representation is pre-aligned to the acquired ultrasound image by performing a calibration to the ultrasound probe.

In one embodiment, the generic grid representation calibration is performed by aligning the top of the ultrasound image with the center of one side of the generic grid representation, and aligning the image plane itself with the plane through the center of the generic grid representation. In one embodiment, the LRS is used for the intraoperative measurements of the undeformed tissue surface. Thus, the pose of the generic grid representation is defined by the same tracking information which defines the pose of the ultrasound image, wherein the tracking information is an optically tracked attached target, or electromagnetically attached tracked target.

In one embodiment, the generic grid representation is represented by a mesh comprising nodes in the form of a generic block.

At step 140, boundary conditions to the mathematical model of tissue biomechanics represented by the generic grid representation are determined. In one embodiment, the boundary conditions are determined using the undeformed tissue surface in conjunction with the position and orientation of the ultrasound probe to estimate a depth to which the tissues are compressed, where the depth is computed by casting rays down from each point of the cloud obtained by the surface acquiring device in the depth direction, and finding an average length of the ray segments which intersect with the probe surface. In another embodiment, the boundary conditions is determined using the location of the ultrasound probe as defined by tissue contact determined by detection within the ultrasound image in conjunction with the final position and orientation of the ultrasound probe at the time of subsurface tissue structure visualization to estimate a depth to which the tissues are compressed, wherein the depth is computed by estimating compression depth as determined by analyzing the difference in the probe location between the initial tissue contact and the final structure visualization.

In one embodiment, the depth is used to assign Dirichlet boundary conditions to the block mesh.

In one embodiment, the boundary conditions for the mathematical model associated with the generic grid representation are assigned such that the far-field face of the generic grid representation is fixed, and the superior and side surfaces are stress-free.

At step 150, the mathematical model of tissue biomechanics for 3D displacements in the generic grid representation of the tissues is solved. The mathematical model of tissue biomechanics is governed by equations (1) and (2) below.

At step 160, the correction of tissue compression is performed by using the reversed and interpolated 3D displacement field on the acquired ultrasound image.

Figure 2:
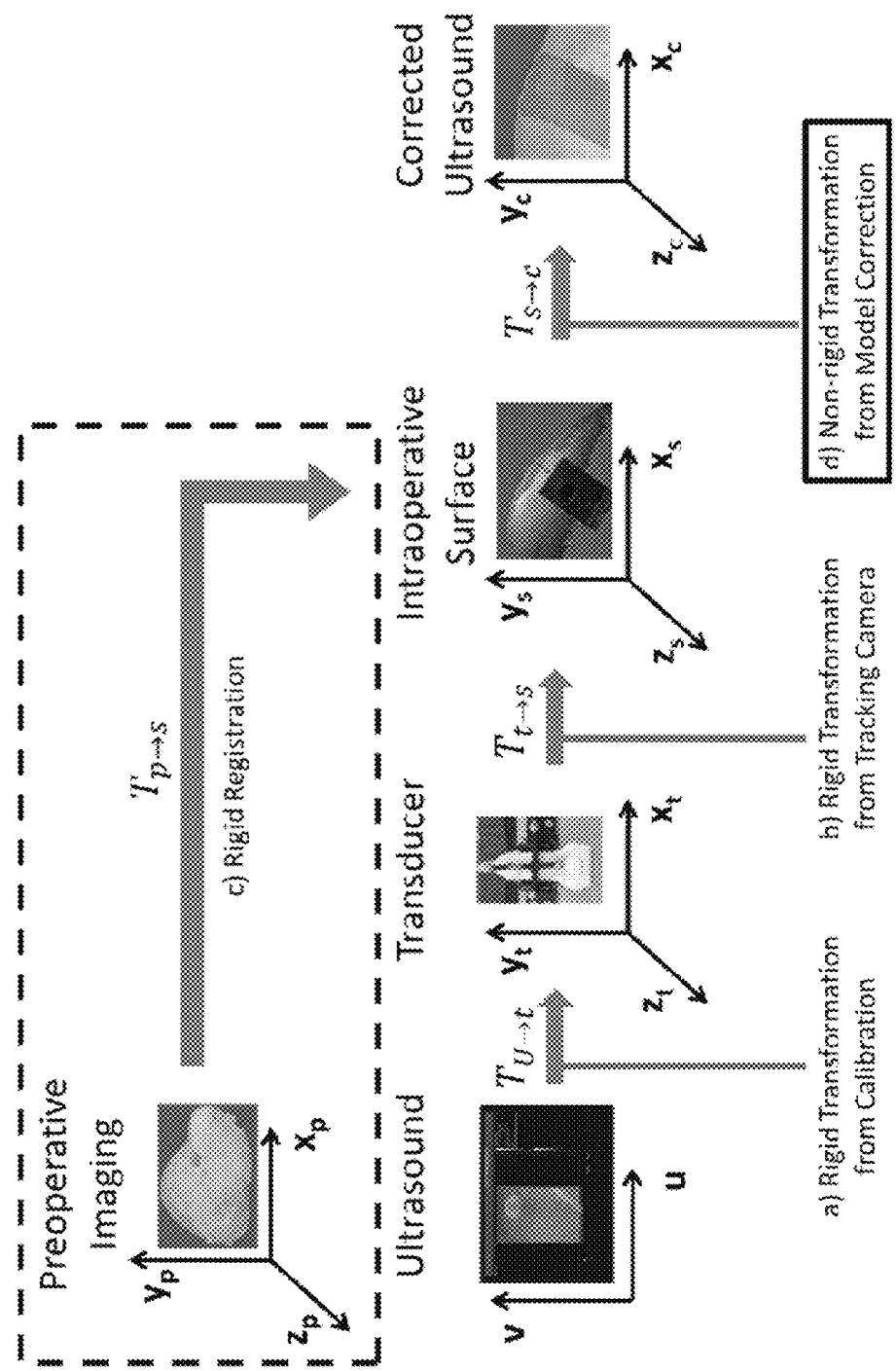
FIG. 2 shows schematically a clinical workflow for the compression correction method according to one embodiment of the invention. The ultrasound data is calibrated to a tracked target attached to the probe (a), which is tracked intraoperatively (b) with a tracking system. A surface digitization tool such as an LRS is also tracked in a consistent coordinate system, and in the patient-specific method this surface information is registered to the preoperative data (c), which is an optional step in the generic correction method (denoted by the dashed box). The surface is also used to calculate the compressive depth for the model to correct the deformed ultrasound data (d), and it is this step that is the key difference between the two compared methods (denoted by the solid box).

The compression compensation method is one step within a pipeline for image-guidance using tracked ultrasound. A brief description of the pipeline is displayed in FIG. 2 to provide context for the compression compensation method and to indicate the difference between the generic approach and the patient-specific model. In certain embodiments, the input data to the generic method are original ultrasound images showing compressed tissue, a calibrated and tracked ultrasound probe, a surface from some other intraoperatively tracked instrumentation, and a biomechanical tissue model used to warp the ultrasound data to show the tissue in an uncompressed state. The patient-specific method also requires an additional registration to preoperative imaging to perform this correction. Each of the correction steps for workflow in FIG. 2 is described in more detail below.

Preoperative Imaging and Patient Model

Image-guided interventions often begin with acquisition of high resolution CT or MR image volumes prior to the procedure. The patient-specific compression correction method utilized a patient model created from these images. However, these data are unnecessary for the generic method of this invention. The specific details of the model-creation for the phantom and clinical studies are described later in the respective experimental sections.

Intraoperative Data Collection

The intraoperative data includes ultrasound images which are captured onto a host computer, along with position and orientation information from an optically tracked target that is attached to the ultrasound probe. After a calibration procedure, which is described below in the phantom experiments, the pose of the ultrasound images are therefore known in the coordinate system of the tracking device. In certain embodiments, other tracked devices, such as a tracked stylus or laser range finder devices, can also be utilize to provide physical measurements in the same coordinate frame.

Compression Correction

Figure 3:
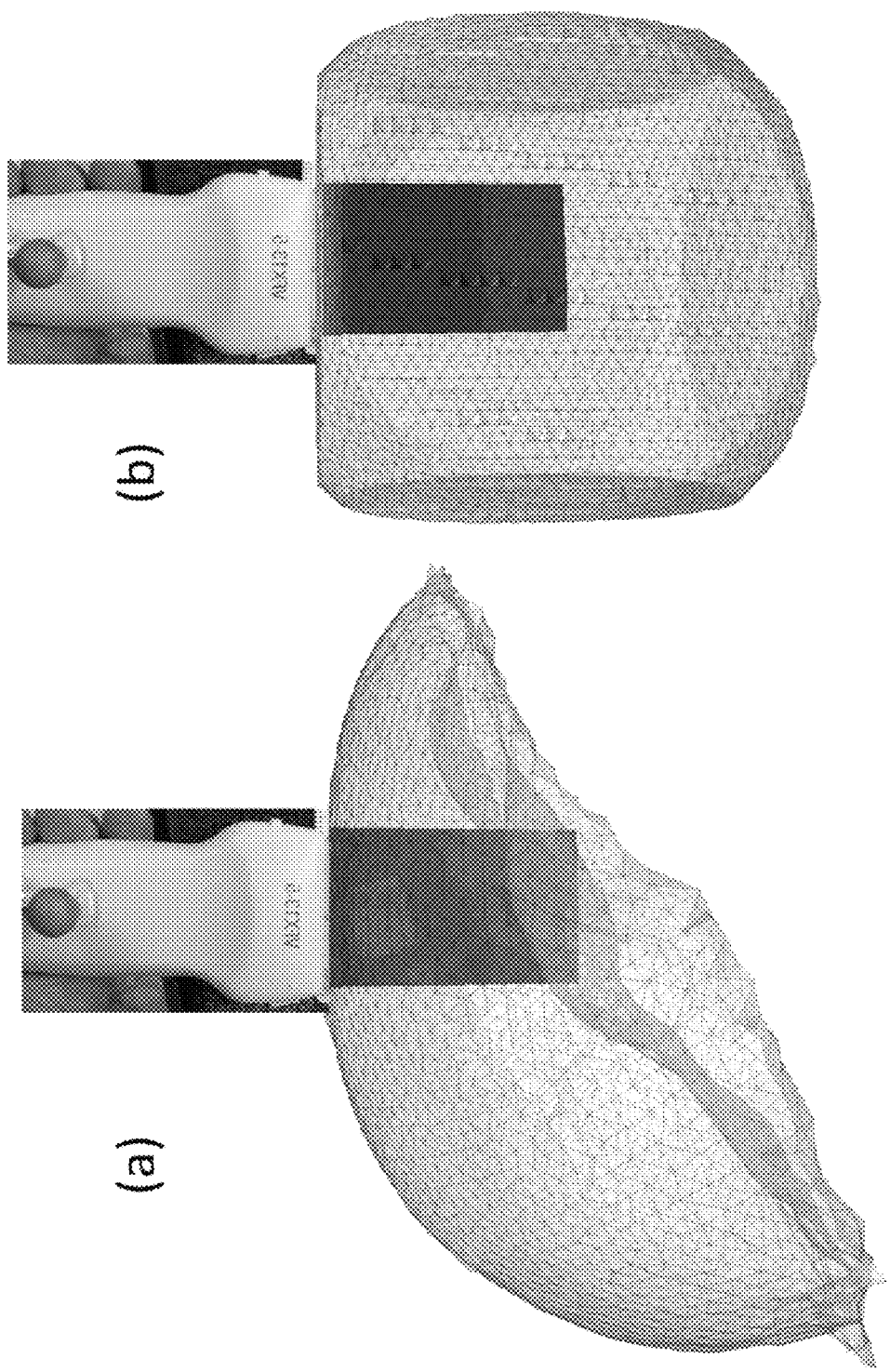
FIG. 3 shows an example of a mesh used for the patient-specific model correction method (a), constructed from preoperative imaging and aligned to the ultrasound data using intraoperative registration methods, and an example of a block mesh for the generic model correction method (b), which is pre-aligned to the ultrasound data by performing a calibration to the ultrasound probe.

According to the invention, the goal of the compression compensation method is to reduce the localization error of soft-tissue subsurface structures as visualized by ultrasound imaging arising from soft tissue deformations exerted by the probe itself. In one aspect, the patient-specific compression compensation method utilizes both probe tracking information in combination with a co-registered patient model in order to estimate the compression depth of the probe into the tissue during insonation, and then to use that depth to correct the tracked ultrasound image poses using a biomechanical model-based approach. In another aspect, the generic compression compensation method does not use a patient-specific model derived from preoperative imaging, but instead uses a generic model to drive the correction as shown in FIG. 3. A summary of the patient-specific method is described in the next subsection, followed by a description of the generic method.

Patient-Specific Correction

The patient-specific compression correction method makes several key assumptions in order to compute a reasonable correction. The primary assumption is that intraoperative ultrasound data could be aligned to the preoperative imaging with an initial rigid registration. The second assumption is that the tissue presentation in terms of mechanical state in the preoperative imaging is similar to the intraoperative presentation, in the absence of tissue manipulation by the ultrasound probe. These two assumptions led to the next assumption, which is that in the presence of tissue compression by the ultrasound probe, the tip of the probe would be some distance below the surface of the co-registered patient model depending on the magnitude of compression.

The strategy is to use the position of the probe tip within the biomechanical tissue model in order to estimate the tissue deformation resulting from application of the probe and then use this data to correct every acquired ultrasound image. The geometry of the probe tip is constructed by scanning it with the LRS, thus providing a digital probe surface model. The probe is tracked in the physical space using a tracked target attached to the probe. The next assumption is that during imaging the user would press the probe only in the depth direction of the ultrasound plane into the tissue, with no lateral or out-of-plane movement (no dragging effects). This assumption is made to simplify the next step of the correction which is to assign boundary conditions to the biomechanical tissue model using the pose of the probe geometry. Assuming purely depth compression, the model surface nodes directly above the digital probe surface are assigned Dirichlet boundary conditions corresponding to the compression vectors calculated from the patient surface to the probe surface. The rest of the patient model is assigned a set of initial boundary conditions based upon the surgical plan and prior knowledge of the patient presentation. In the case of the liver phantom, the inferior surface is fixed as it is on a rigid conforming base, and the superior surface is set to stress free boundary conditions and allowed to freely deform. In the case of the clinical brain case, the mesh nodes corresponding to the craniotomy region are set as stress free, the base of the brain is set as fixed, and the rest of the brain nodes are set to have zero displacement in the normal direction but stress free in the tangential directions to allow for slipping along the skull. These boundary conditions have been used in brain models previously for model-updated image guided surgery [8, 9].

After the assignment of boundary conditions, the model is solved for 3D displacements over the entire mesh to estimate the probe-deformed state of the tissue. The model used in both methodologies is the standard 3D Navier-Cauchy equations for the displacement field:

$$\frac{E}{2(1+v)}\nabla^2 u + \frac{E}{2(1+v)(1-2v)}\nabla(\nabla \cdot u) = 0 \quad (1)$$

where E is Young's modulus, v is Poisson's ratio, and u is the 3D displacement vector at a point in the tissue. The partial differential equation is solved within a finite element method framework using the Galerkin weighted residual technique with linear basis functions. The system of equations that solves for the displacement vectors at every node in the mesh can be written as:

$$[K]\{u\}=\{f\} \quad (2)$$

where K is the global stiffness matrix, u is the vector of nodal displacements, and f contains the contributions of boundary conditions. For each ultrasound image to be corrected, this system of equations is constructed and solved for the nodal displacements which satisfy static equilibrium for the supplied boundary conditions. These displacements are then reversed and interpolated onto the tracked ultrasound data, which is then deformed with this 3D displacement field to an estimate of its state in the absence of compression. It should be noted that there are important implications to the nature of this patient-specific computation with respect to encumbrance that will be discussed in comparison to the generic model of the invention in the next section.

Generic Correction

The first difference between the generic correction and the patient-specific correction is that instead of a patient-specific mesh constructed from preoperative imaging and registered to intraoperative space, the generic method uses a pre-constructed block mesh, as shown in FIG. 3, which is calibrated to follow the tip of the tracked ultrasound probe. The most important consequence of this framework is that the generic method only requires a sparse intraoperative measurement of tissue compression in order to provide a model correction, rather than a registration to preoperative imaging. This could be either provided by having separate digitization of the surface in physical space (e.g., a laser range scan of the surface of interest) or would need a trigger to track ultrasound position once in contact with the tissue. In one embodiment, the former is utilized. Additionally, it should be noted that a pre-computed mesh in this instance is possible and offers distinct computational advantages that are described later below.

Figure 4:
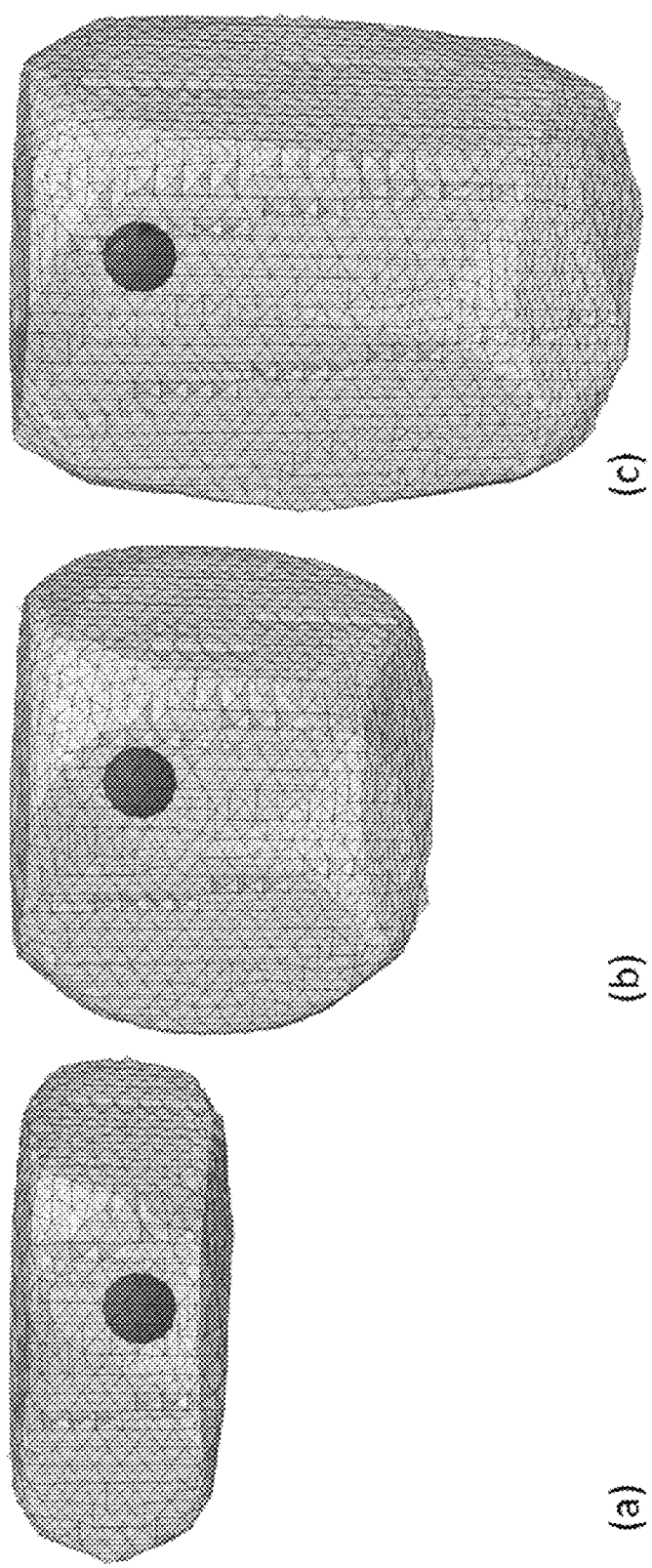
FIG. 4 shows examples of the meshes used in the simulation studies with sizes of 10×10×5 cm (a), 10×10×10 cm (b) and 10×10×15 cm (c). In this case, a simulated 20 mm diameter tumor is shown at the equivalent 3 cm depth in each mesh.

The block mesh calibration procedure simply requires the alignment of the top of the ultrasound image with the center of one side of the mesh, and of the image plane itself with the plane through the center of the block. The pose of the generic block mesh thus is defined by the same tracking information which defines the pose of the ultrasound image, i.e., the optically tracked attached target in this exemplary embodiment. In this realization, the general strategy is to acquire intraoperative measurements of the undeformed tissue surface using an LRS, and then use that surface in conjunction with the location of the ultrasound probe to estimate the depth to which the tissue is compressed. This depth is computed by casting rays down from each point of the LRS cloud in the depth direction, and finding the average length of the ray segments which intersect with the tracked probe tip surface. This depth is then used to assign Dirichlet boundary conditions to the block mesh in a similar manner as the patient-specific correction, although with a slight difference. The initial boundary conditions for the mesh in this method are assigned such that the far-field face of the block mesh is fixed, and the superior and side surfaces are stress-free. This is one of the key assumptions of this method, far-field deformations are near zero. This certainly represents a potential source of error depending on the angle of insonation, the location on the organ, and the size of the organ. One way to mitigate this is to pre-compute multiple tissue blocks with differing far-field lengths, as shown in FIG. 4. Similar to how ultrasound transducers can have different fields of view that can be selected by the user, it is envisioned that a user could select a correction far-field assumption based on in vivo conditions at the time of interrogation. This is a central reason for examining the effects of differing far-field assumptions in the experiments described further below.

Nevertheless, after assignment of boundary conditions, the model is solved for 3D displacements in the block of tissue, and the displacements are reversed and interpolated onto the ultrasound data to perform the correction. The model construction is governed by the same constitutive equations given by (1) and (2). However, there are several advantages that the generic correction offers compared to the patient-specific model. With respect to the patient-specific method, the global stiffness matrix, K, would need to be reconstructed whenever different regions of the organ boundary are engaged for imaging, i.e., with the application of Dirichlet boundary conditions at different nodes based on localization, the stiffness matrix would need to be altered, such as from a displacement to a stress-free condition or vice versa. While all equations for every boundary node could be stored to prevent repeating element assembly, preconditioners would likely need to be recomputed followed by iterative matrix solutions. This would be an expensive process especially if trying to achieve frame rate updates. One strategy would be to use force-based boundary conditions which would allow for a great deal of pre-computation but would require accurate measurement of applied force as well as material properties of the tissue [3, 4]. With respect to the generic correction, however, the type of boundary condition assigned to each boundary node will always remain the same, as each correction proceeds by merely altering the magnitude of the displacement boundary conditions on the top of the block mesh. Thus, it is possible to pre-compute K and reuse it for each correction whenever f is updated in a simple matrix multiplication:

$$\{u\}=[K]^{-1}\{f\} \quad (3)$$

Another property of the generic method offers a further computational speedup. In order to correct the ultrasound data, only the model solution at a plane of the mesh which corresponds to the ultrasound image plane is actually needed. The computations solving for the rest of the mesh node displacements are not essential but only their influence on the localization information within the slice itself is needed. This makes it desirable to somehow eliminate the computational burden of those nodes from the system of equations during surgery. This can be accomplished through the method of condensation which results in a smaller system of equations that can be solved much more rapidly [10]. The first step in this process is to carefully arrange the ordering of the mesh node indices to ensure that the first N equations belong to the nodes lying on the ultrasound plane, as well as any nodes on the top surface which are assigned varying amounts of compression boundary conditions. Assuming this ordering, the equation from (2) can be rewritten as a block matrix system where the subscripts p and a indicate the plane nodes and all other nodes, respectively:

$$\begin{bmatrix} K_{pp} & K_{pa} \\ K_{ap} & K_{aa} \end{bmatrix} \begin{Bmatrix} u_p \\ u_a \end{Bmatrix} = \begin{Bmatrix} f_p \\ f_a \end{Bmatrix} \quad (4)$$

The block matrix system in equation (4) can be rearranged to a form involving only the displacement solution of the plane nodes, $u_p$:

$$[\check{K}_{pp}][u_p] = \{\check{f}_s\} \quad (5)$$

where $$[\check{K}_{pp}] = [K_{aa}] - [K_{pa}][K_{aa}]^{-1}[K_{ap}] \quad (6)$$

$$\{\check{f}_s\} = \{f_s\} - [K_{pa}][K_{aa}]^{-1}\{f_a\} \quad (7)$$

The modified stiffness matrix given in equation (6) represents a transfer of the displacements from all non-plane nodes to the plane nodes which are the primary concern, and maintains the volumetric nature of the model. Using this stiffness matrix offers significant computational benefit because it is a fraction of the size of the full K matrix. It can be similarly pre-computed and stored for very fast solutions of the $u_p$ vector of plane node displacements. In addition, given the careful ordering of the node indices explained above and the assignment of initial boundary conditions, it will also be the case that all nodes in the $f_a$ vector will always be assigned either zero stress or zero displacement boundary conditions. Given in equation (7), this implies that changes in the compression depth during imaging will result in simple reassignment of the values in $\check{f}_s$:

$$\{\check{f}_s\}\big|_{\{f_a\}=0} = \{f_s\} \quad (8)$$

Given the pre-computation of the modified stiffness matrix in equation (6) and the speed of assigning new values in equation (8), the generic method offers a very large speed increase compared to the patient-specific method and can potentially be performed at near real-time frame rates.

According to certain embodiments of the invention, experimental results with gel phantoms demonstrated that the generic method reduced the mock tumor margin Modified Hausdorff Distance (MHD) from about 5.0±1.6 mm to about 2.1±0.7 mm, and reduced mock tumor centroid alignment error from about 7.6±2.6 mm to about 2.6±1.1 mm. The method was applied to a clinical case, and reduced the in vivo tumor margin MHD error from about 5.4±0.1 mm to about 2.9±0.1 mm, and the centroid alignment error from about 7.2±0.2 mm to about 3.8±0.4 mm. Thus, the invented method can effectively improve alignment of ultrasound and tomographic images, and is more efficient compared to a previously reported patient-specific compression correction [5].

It should be noted that all or a part of the steps according to the embodiments of the present invention is implemented by hardware or a program instructing relevant hardware.

In one aspect of the invention, a system for real-time correction of tissue compression for tracked ultrasound includes an ultrasound probe, a surface acquiring device such as an LRS or a stereo pair camera set, a tracking device and a controller coupled with the ultrasound probe, the surface acquiring device and the tracking device.

The ultrasound probe is configured to acquire an ultrasound image of tissues of interest. In one embodiment, ultrasound probe is tracked by the tracking device with a tracked attached target to provide a position and an orientation of the probe surface of the ultrasound probe for the acquired ultrasound image.

The surface acquiring device is configured to perform intraoperative measurements of the undeformed tissue surface as so to construct a block mesh of the tissues. In one embodiment, the surface acquiring device is further configured to construct a digital representation of the probe surface.

The tracking device configured to track the ultrasound probe and the surface acquiring device.

The controller is configured to construct a generic grid representation of tissues for use with a mathematical model of tissue biomechanics, wherein the generic grid representation is pre-aligned to the acquired ultrasound image by performing a calibration to the ultrasound probe; solve the mathematical model of tissue biomechanics for three-dimensional (3D) displacements in the generic grid representation of the tissues, and perform the correction of tissue compression by using the reversed and interpolated 3D displacement field onto the acquired ultrasound image.

Further, the controller is configured to calibrate the ultrasound image to the tracked attached target, so that the pose of the ultrasound image is defined in the coordinate system of the tracking device.

Moreover, the controller is configured to determine boundary conditions using the undeformed tissue surface in conjunction with the position and orientation of the ultrasound probe to estimate a depth to which the tissues are compressed, wherein the depth is computed by casting rays down from each point of the cloud obtained by the surface acquiring device in the depth direction, and finding an average length of the ray segments which intersect with the probe surface.

In addition, the controller is configured to determine boundary conditions using the undeformed tissue surface as determined by recording the orientation and position of the ultrasound probe at first contact with the tissue in the ultrasound image in conjunction with the position and orientation of the ultrasound probe when placed to visualize the subsurface target, wherein the difference in these positions is used to estimate a depth to which the tissues are compressed.

The system may further comprise a display for displaying at least the ultrasound image, the generic grid representation of the tissues, and the correction of tissue compression.

In one aspect, the invention relates to a non-transitory computer-readable medium/memory which stores computer executable instructions or program codes. The computer executable instructions or program codes enable a controller, such as a computer or a similar computing system to complete various operations in the above disclosed method.

In one embodiment, the functions comprises calibrating an ultrasound image acquired with an ultrasound probe to a tracked target attached to the ultrasound probe; cacquiring intraoperative measurements of the undeformed tissue surface; constructing a generic grid representation of tissues for use with a mathematical model of tissue biomechanics, wherein the grid representation is pre-aligned to the acquired ultrasound image by performing a calibration to the ultrasound probe; determining boundary conditions to the mathematical model of tissue biomechanics represented by the generic grid representation; solving the mathematical model of tissue biomechanics for three-dimensional (3D) displacements in the generic grid representation of the tissues; and performing the correction of tissue compression by using the reversed and interpolated 3D displacement field onto the acquired ultrasound image.

In one embodiment, the function of determining the boundary conditions comprises the function of using the undeformed tissue surface in conjunction with the position and orientation of the ultrasound probe to estimate a depth to which the tissues are compressed, wherein the depth is computed by casting rays down from each point of the cloud obtained by the surface acquiring device in the depth direction, and finding an average length of the ray segments which intersect with the probe surface.

In one embodiment, the function of determining boundary conditions comprises using the undeformed tissue surface as determined by recording the orientation and position of the ultrasound probe at first contact with the tissue in the ultrasound image in conjunction with the position and orientation of the ultrasound probe when placed to visualize the subsurface target, wherein the difference in these positions is used to estimate a depth to which the tissues are compressed.

The storage medium/memory may include, but is not limited to, high-speed random access medium/memory such as DRAM, SRAM, DDR RAM or other random access solid state memory devices, and non-volatile memory such as one or more magnetic disk storage devices, optical disk storage devices, flash memory devices, or other non-volatile solid state storage devices.

Without intent to limit the scope of the invention, experimental validations, examples and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Experimental Validations and Results

Simulations

Several simulations were performed to examine the sensitivity of the generic correction method to various factors.

The first simulation performed was to analyze the effect of the finite element mesh resolution on the model correction. This simulation included constructing equivalent 10×10×5 cm block meshes with a tetrahedral element edge length ranging from 2 to 10 mm. The number of nodes in the meshes ranged from 53,018 to 634 between the 2 and 10 mm resolution, respectively. Three simulated tumors were created with diameters of 10, 20, and 40 mm and placed separately in an instance of each mesh. A 10 mm surface compression was then simulated for each mesh and the model solution was interpolated to the tumor nodes for comparison of the effects of the mesh resolution on the correction strategy. The comparison was performed by utilizing the most finely resolved mesh (2 mm edge length) as the ground truth solution, with each subsequent model solution from the coarser meshes being compared to the ground truth solution in terms of the difference in final tumor position.

Figure 6:
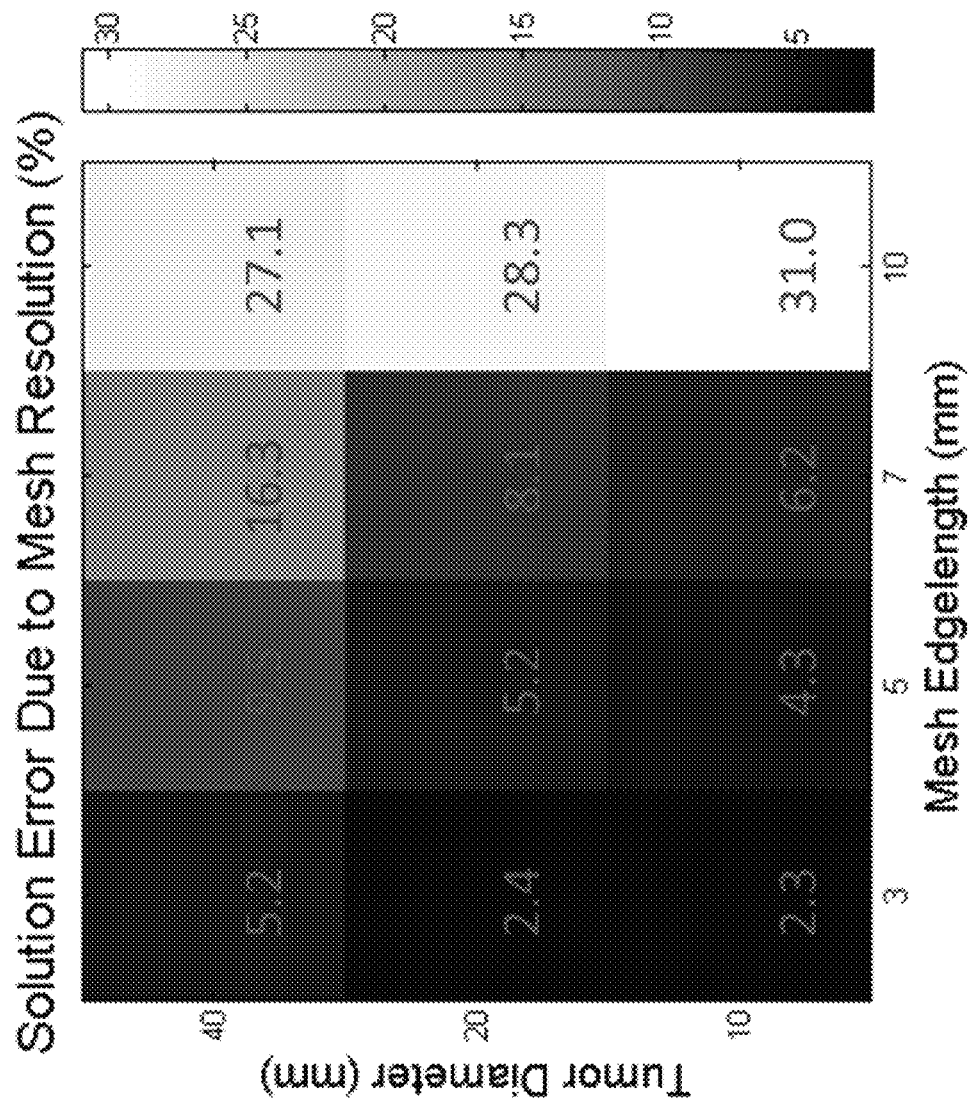
FIG. 6 shows effects of the mesh resolution on three sizes of a tumor after a simulated 10 mm surface compression. The tumor node error is defined relative to the result of the solution of a mesh with 2 mm edge length resolution.

The results of the mesh resolution simulations are shown in FIG. 6. This figure displays how the model solutions at varying mesh resolutions changes compared to the solution to the high resolution mesh using a 2 mm element edge length. The general trend in each case was that as the mesh becomes coarser, the interpolated model solution deviates from the solution obtained from the more finely resolved mesh, especially above an edge length of 7 mm.

The second simulation performed was aimed at determining the potential effects of the following variables upon the correction: 1) the block mesh size, 2) the tumor stiffness, and 3) the tumor size. Three block meshes were created with dimensions of 10×10×5 cm, 10×10×10 cm, and 10×10×15 cm constructed with 5 mm edge length. Three simulated tumors were created with diameters of 10, 20, and 40 mm and each placed at a 3 cm depth (half the maximum depth of the linear array probe used for the phantom and clinical data in this embodiment) in an instance of each block mesh described above. To illustrate, the 20 mm tumor is shown in the meshes of different sizes in FIG. 4. The tumors were assigned stiffness values of 1:1, 10:1, and 30:1 compared to the rest of the tissue block, resulting in 27 meshes (three mesh sizes, three tumor sizes, and three stiffness ratios). Each mesh was then subjected to surface compression ranging from 0 to 10 mm. For each state of compression, the model-deformed tumor surfaces were compared to the uncompressed tumor surfaces to illustrate the effect of tumor stiffness and size on the model solution, which would in turn affect the correction.

Figure 7:
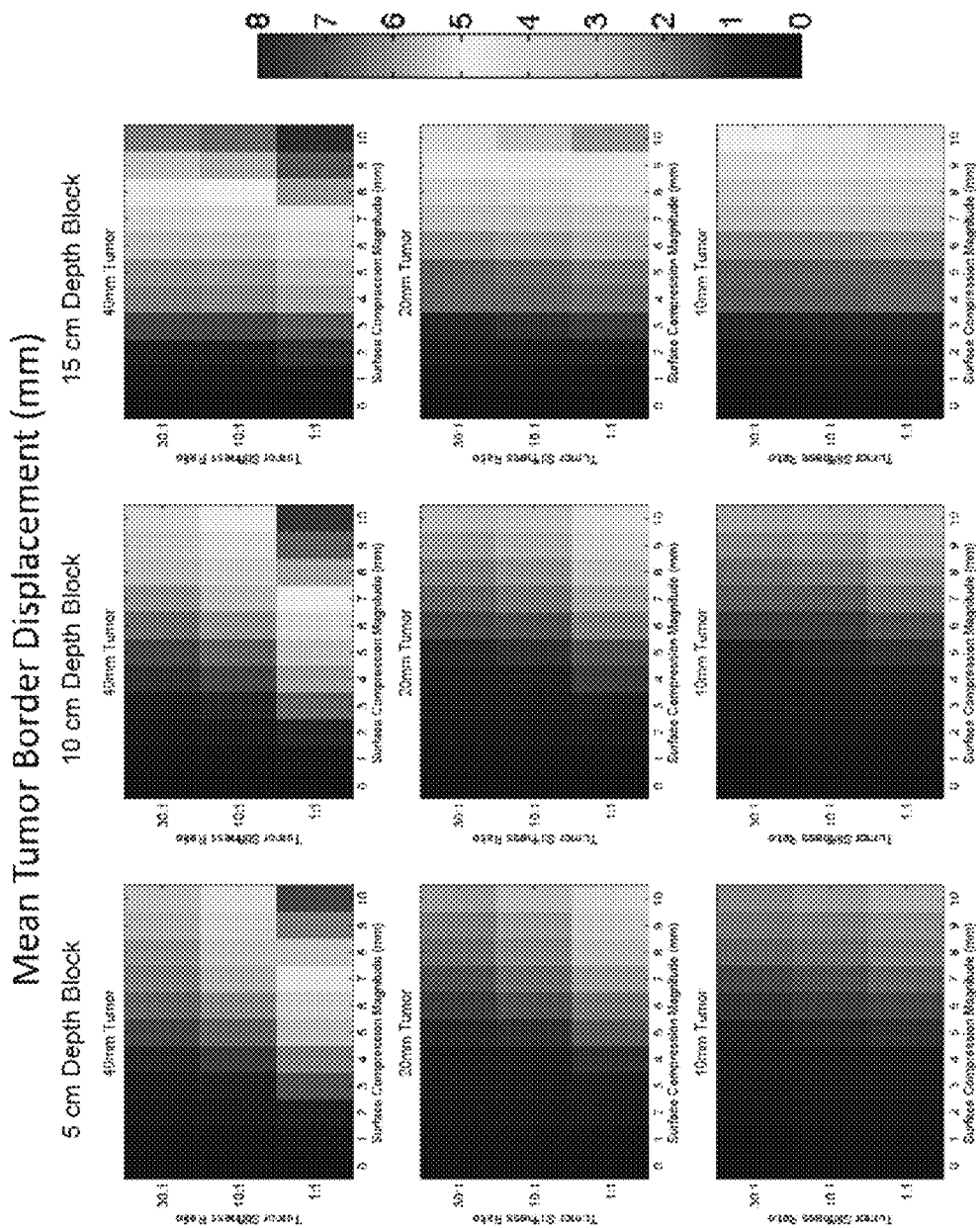
FIG. 7 shows effects of block mesh depth, tumor stiffness, and tumor size upon the model-predicted tumor border deformation under varying amounts of surface compression (colorbar is in millimeters).

The results of the second simulation testing the effects of mesh size, tumor stiffness, and tumor size are shown in FIG. 7. Each graph shows that as the applied surface compression increases, the tumor boundary nodes displace correspondingly. It is seen that compression is communicated to the tumor boundary displacement more effectively as the tumors decrease in stiffness with larger distortions experienced by larger tumors (which is expected, i.e., softer materials would experience larger shape distortion). Looking across depth block sizes, it is seen that the tumor boundary experiences more displacement with increasing block depth. This is expected as the far field fixed displacement will inhibit internal block motion less in larger depth blocks. However, looking at the top subfigures in FIG. 7, more pronounced effects from stiffness at large compressions with larger tumors can be seen.

Figure 5:
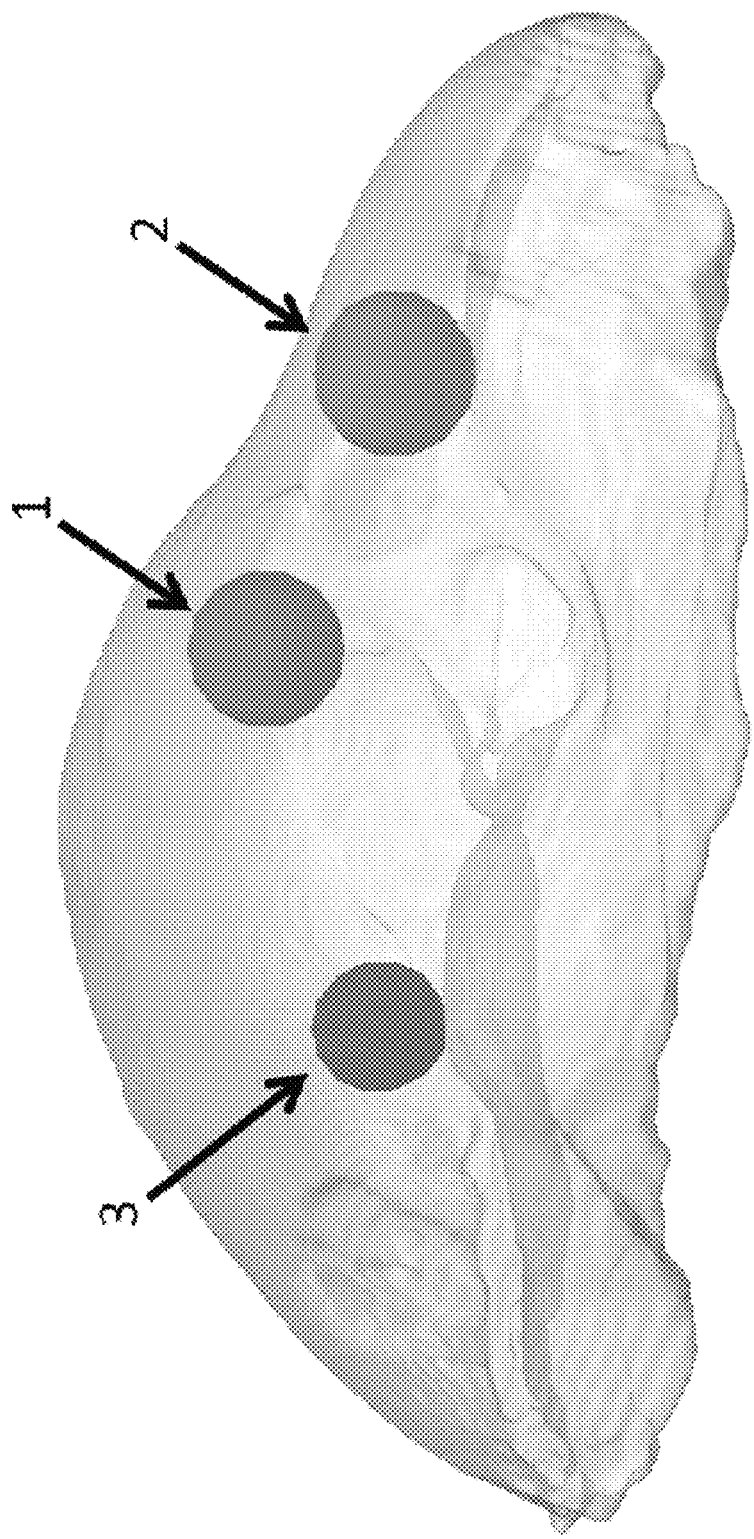
FIG. 5 shows simulated tumor locations, showing a tumor in the middle of the liver (1), in the small left lobe (2), and in the larger right lobe (3).

The third simulation performed was aimed at examining the sensitivity of the generic correction to varying tumor locations within the tissue. An organ-like finite element mesh was first constructed from a CT image volume of a liver phantom. Three 20 min diameter spheres were manually inserted into the mesh at different locations to act as simulated tumors. The three locations are shown in FIG. 5, and were chosen to demonstrate that the generic correction method improves subsurface target localization regardless of the local organ geometry involved. In the case of each tumor, a surface compression of 1 cm was simulated using the liver mesh to compress the tumor, and then the generic correction method was used to correct the deformed tumor using a 10×10×10 cm block mesh. The generic corrected tumors were then each compared to the original uncompressed spheres in terms of boundary node error and tumor centroid error.

Figure 8:
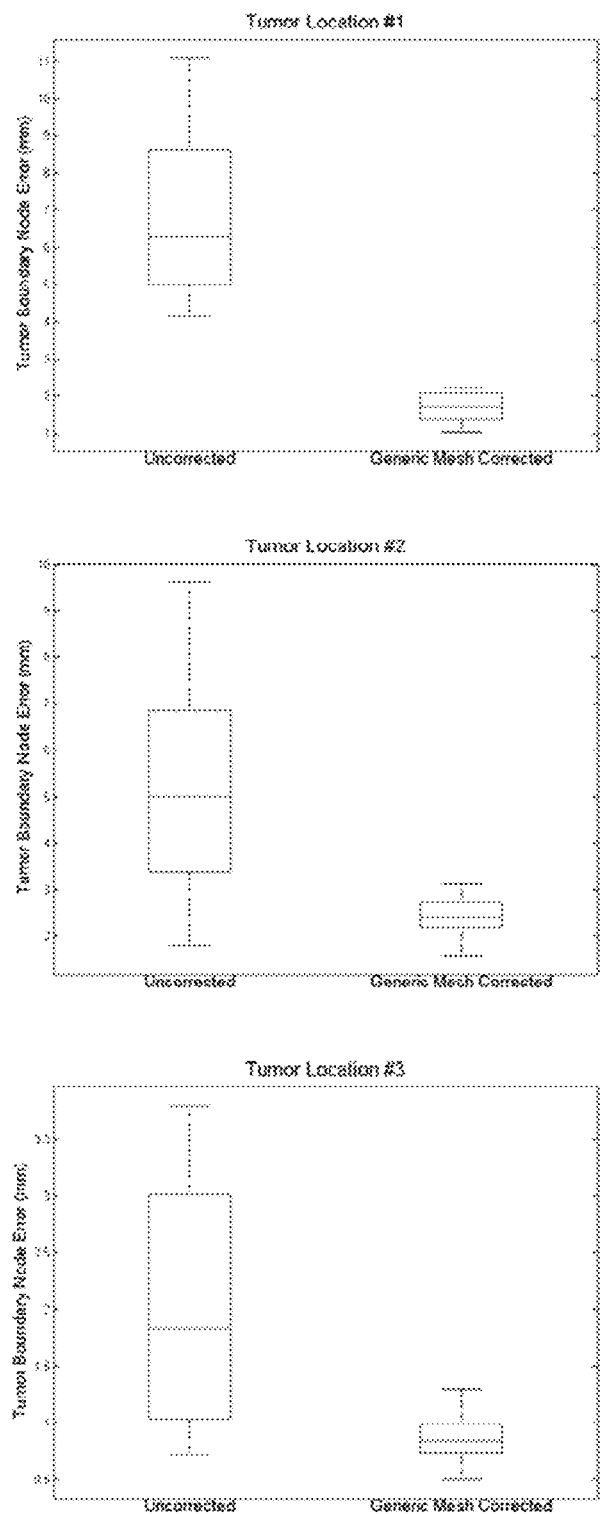
FIG. 8 shows effects of tumor location on generic block mesh correction improvement in three simulated tumors (number of tumor boundary nodes N=50).

The results of the third simulation testing the effects of tumor location are shown in FIG. 8. This figure shows the tumor boundary node error (for 50 boundary nodes) prior to correction and after application of the generic method. Prior to correction, the centroid error for the compressed tumor in Location 1, 2, and 3 designated in FIG. 5 was 6.7 mm, 5.0 mm, and 2.0 mm, respectively. After correction, the centroid error in location 1, 2, and 3 was 1.6 mm, 1.8 mm, and 0.8 mm, respectively.

Phantom Experiments

A compliant gel phantom was constructed by mixing 7% by mass polyvinyl alcohol (PVA) in water with 10% by volume glycerol. A small amount was poured into a tumor mold and subjected to four freeze-thaw cycles, in which the gel was frozen at −40° C. for 12 hours and then thawed at room temperature for 12 additional hours. The first freeze-thaw cycle produces a gel with a tissue-like consistency, and each additional cycle results in an increasingly stiffer material. The phantom tumor was then suspended by wire in a larger anthropomorphic liver mold with PVA mixture and subjected to one additional freeze-thaw cycle. This resulted in a soft tissue phantom containing a stiffer tumor. The completed phantom was fixed to a rigid base containing fiducials which were used to initialize the image-to-physical registration.

Phantom tomograms were acquired in order to compare the patient-specific and generic correction methods to a ground truth CT image set. CT image volumes were acquired for the phantoms using a clinical CT machine at 512×512×422 with 0.6 mm isotropic voxels. The bulk phantom and tumor were segmented using intensity thresholding in Analyze 9.0 (Mayo Clinic, Rochester, Minn.). Isosurfaces were generated from the segmentations using the marching cubes algorithm and smoothed with a Laplacian filter. A patient-specific finite element mesh with tetrahedral elements was created from the smoothed phantom isosurface using custom-built mesh generation software [11].

The phantom fiducial markers were localized in the physical space with a tracked pointer and an initial rigid point-based registration to the CT images was performed [12]. An LRS scan of the liver surface was acquired and an iterative closest point (ICP) registration was performed of the tracked LRS point cloud to the CT surface in order to refine the registration [13]. This alignment was used to perform the patient-specific correction method and served as the gold standard validation for the generic correction method of this invention.

An Acuson Antares ultrasound machine (Siemens Inc., Munich, Germany) with a VFX13-5 linear array probe at 10 MHz was used to acquire all ultrasound images in this study. The machine was used to collect both B-mode and strain images with the eSie Touch elasticity software from the manufacturer in order to illustrate the general applicability of the correction method to all forms of ultrasound data. The ultrasound images were tracked in 3D space by synchronizing each image with the pose detected by a Polaris Spectra optical tracking system (Northern Digital, Waterloo, ON, Canada) for a passive rigid body attached to the ultrasound probe. The tracked ultrasound probe was calibrated using the method described by Muratore et al. such that all pixels in each image were associated with a 3D pose [14].

In addition to the ultrasound data collected above, the other intraoperative tools used in this study were a tracked pointer and laser range scanner (LRS) [15]. The pointer was used to digitize point fiducials such as beads on the phantom base and craniofacial landmarks on the patient. These points were used to initialize a surface-based registration of the dense point clouds from the LRS to the preoperative patient-specific model in the case of the phantoms.

Tracked B-mode and strain images were acquired of the embedded tumor, and the transformation matrix from the ICP registration was used to automatically align all tracked ultrasound images with the CT data. A total of 178 B-mode and 83 strain images were collected of the tumor. The tracking and registration transformations were then applied to the digital probe surface in order to generate boundary conditions for the two correction methods as described previously.

After the generation of boundary conditions, the patient-specific and generic correction methods were applied to each ultrasound image. This resulted in a collection of uncorrected, patient-specific corrected, and generic corrected images. With respect to the generic correction, a 10×10×10 cm block mesh was used. For both methods, the meshes were assigned a tumor Young's modulus ratio of 1:1 with Poisson's ratio at 0.49 because PVA is known to be nearly incompressible. Each population of images was compared to the baseline CT images in terms of tumor geometry in order to evaluate the corrections. The tumor borders in each B-mode and strain image were segmented semi-automatically using the Livewire technique, and for each ultrasound image the CT volume was re-sliced to provide a co-planar CT slice and tumor contour corresponding to the 3D pose of the co-registered ultrasound slice. The tumor borders from ultrasound and CT were then compared in terms of Modified Hausdorff Distance (MHD) and centroid distance between the two contours [16]. The MHD and centroid error metrics were computed prior to and after each correction, and were the primary metrics in determining the efficacy of the methods.

Figure 9:
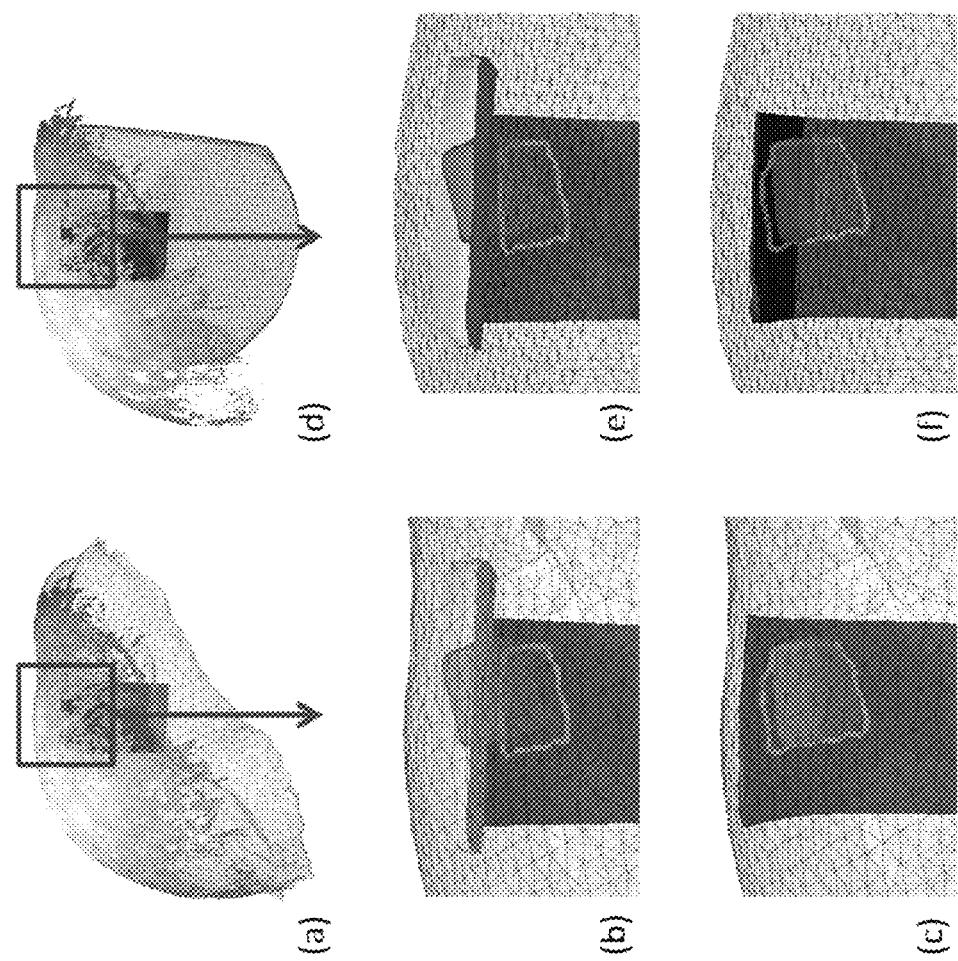
FIG. 9 shows an example of B-mode image slice correction with the patient specific-model correction (a)-(c) and generic model correction (d)-(f). (a) and (d) show the co-registered LRS point cloud on the respective mesh, (b) and (e) show the tracked probe surface and the misalignment between the ultrasound tumor border with the CT tumor, and (c) and (f) show the corrected ultrasound image.

The patient-specific and generic model corrections were deployed in the liver phantom, and an example of the correction process applied to a tracked ultrasound slice is shown in FIG. 9. Qualitatively, there was a clear improvement to the alignment between ultrasound and co-registered tomograms in the phantom experiments. In addition, the ultrasound contours corrected with the generic model method were very geometrically similar to the ultrasound contours corrected with the patient-specific method. It should be noted that difference in contour and green rendered object in FIGS. 9(b) and 9(e) represents the error in object localization and shape if no correction is performed.

Figure 10:
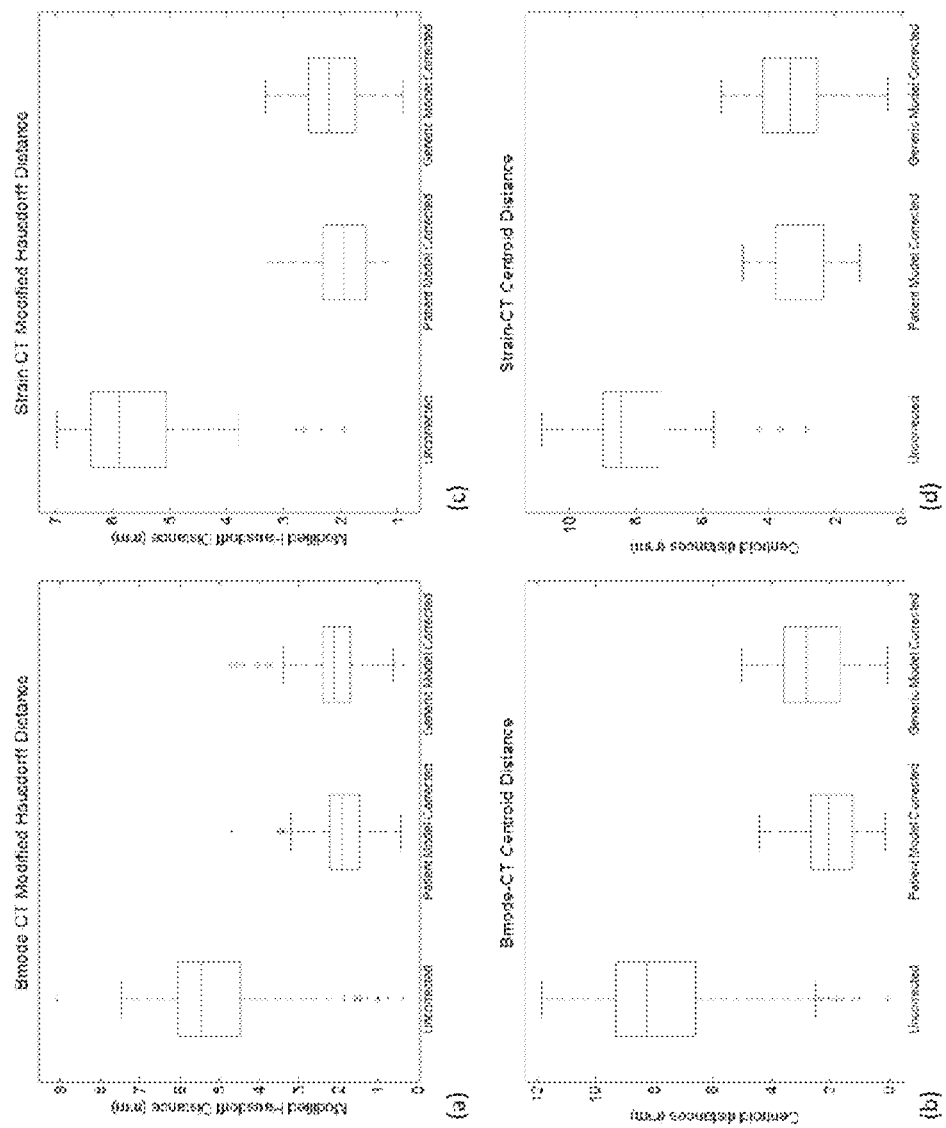
FIG. 10 shows alignment error results for the B-mode (a) and (b) and strain imaging (c) and (d) modalities for the organ-like phantom (n=178 for B-mode, and n=83 for strain). The position of tumor borders in each modality was evaluated in terms of Modified Hausdorff Distance to the co-aligned CT borders (a) and (c), as well as the distance between the centroid of the ultrasound tumor with the co-planar CT tumor border (b) and (d). The edges of the boxes are the 25th and 75th percentiles, and the whiskers extend to the most extreme data points not considered as outliers.

The quantitative results of the phantom experiments in FIG. 10 show the MHD and co-planar-centroid distances as error metrics in comparing the ultrasound tumor borders with the co-registered CT borders, for both B-mode and strain images. The B-mode MHD values for the uncorrected, patient-specific corrected, and generic corrected tumor borders were 5.0±1.6 mm, 1.9±0.6 mm, and 2.1±0.7 mm, respectively. A Wilcoxon signed rank test was computed for the null hypothesis that the median difference between the error metrics was zero. It was found that there was a statistically significant difference between each of the image populations using this metric ($p<0.01$). The B-mode centroid error values for the uncorrected, patient-specific corrected, and generic corrected tumor borders were 7.6±2.6 mm, 2.0±0.9 mm, and 2.6±1.1 mm, respectively. The Wilcoxon test again found the three image populations to be significantly different from one another based on this metric ($p<0.01$).

With respect to the strain images, the strain MHD values for the uncorrected, patient-specific corrected, and generic corrected tumor borders were 5.6±1.1 mm, 2.0±0.5 mm, and 2.2±0.5 mm, respectively. The Wilcoxon test found all three image populations to be statistically different using the MHD metric ($p<0.01$). The strain centroid error values for the uncorrected, patient-specific corrected, and generic corrected tumor borders were 8.0±1.6 mm, 3.0±0.9 mm, and 3.3±1.1 mm, respectively. The Wilcoxon test also found all three image populations to be statistically different using the centroid error metric (p<0.01).

Clinical Case

The patient-specific and the generic correction methods were deployed in a preliminary clinical case. The clinical dataset included a meningioma patient at Vanderbilt Medical Center. Informed written consent was obtained from the patient prior to the study with the approval of Vanderbilt University Institutional Review Board. The preoperative MR volume was segmented to produce brain and tumor surfaces, which were used to create a patient specific model in the same manner as the phantom data. With respect to the generic correction, a 10×10×10 cm block of tissue was used. The tumor in this case was a meningioma located superficially on the left side. In this case the tumor and brain were assigned a 1:1 stiffness ratio and Poisson's ratio of 0.45 [17]. Alignment of the intraoperative tracked ultrasound images to the MR was performed by scanning the face of the patient with the LRS and performing an ICP registration between the LRS face point cloud and the MR patient model. There was no LRS cloud of the brain surface available in the case of this specific patient, and so a random sampling of the MR model surface was used to simulate LRS data in that case. Tracked B-mode images were obtained immediately after the craniotomy. Both correction methods were then applied to the ultrasound data and compared to the co-aligned MR tumor borders in terms of the co-planar contour MHD and centroid error.

Figure 11:
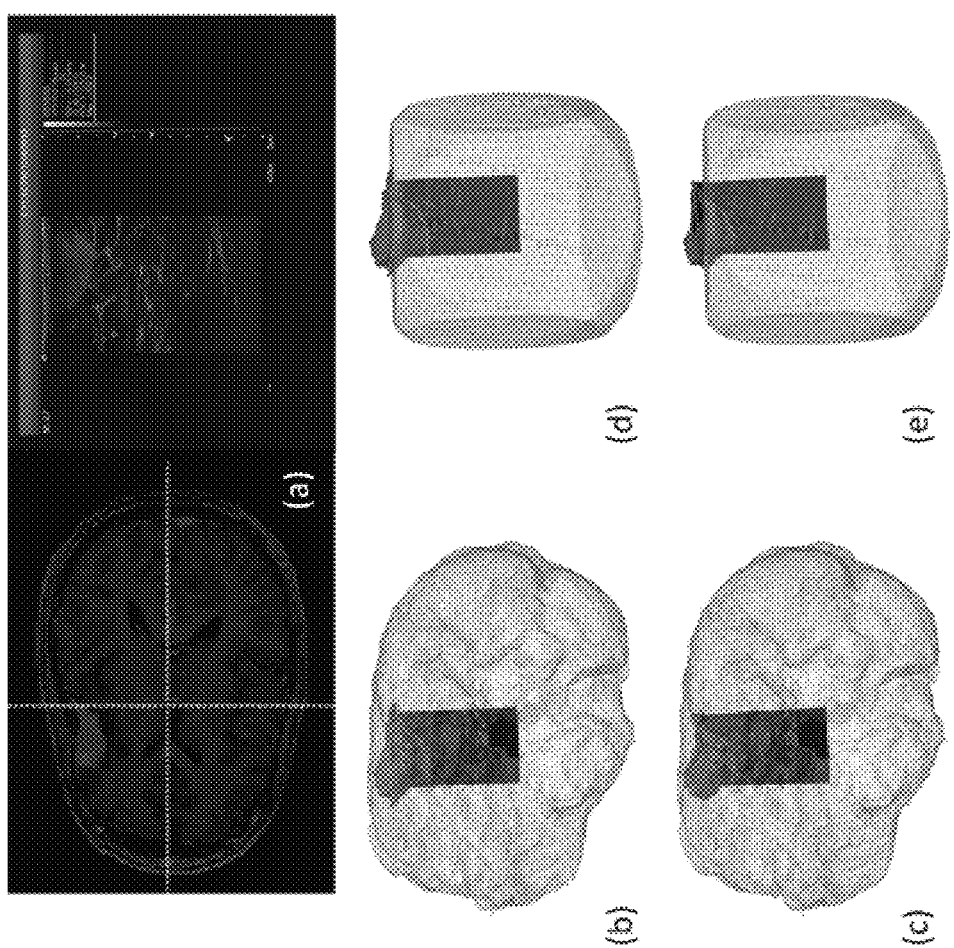
FIG. 11 shows an example of the patient images of a superficial tumor visible in MR and B-mode (a) and the patient-specific correction (b) and (c) and generic model correction (d) and (e) applied to a B-mode image slice for the clinical case. (b) and (d) show the tracked probe surface and the misalignment between the ultrasound tumor border with the CT tumor, and (c) and (e) show the corrected ultrasound image.
Figure 12:
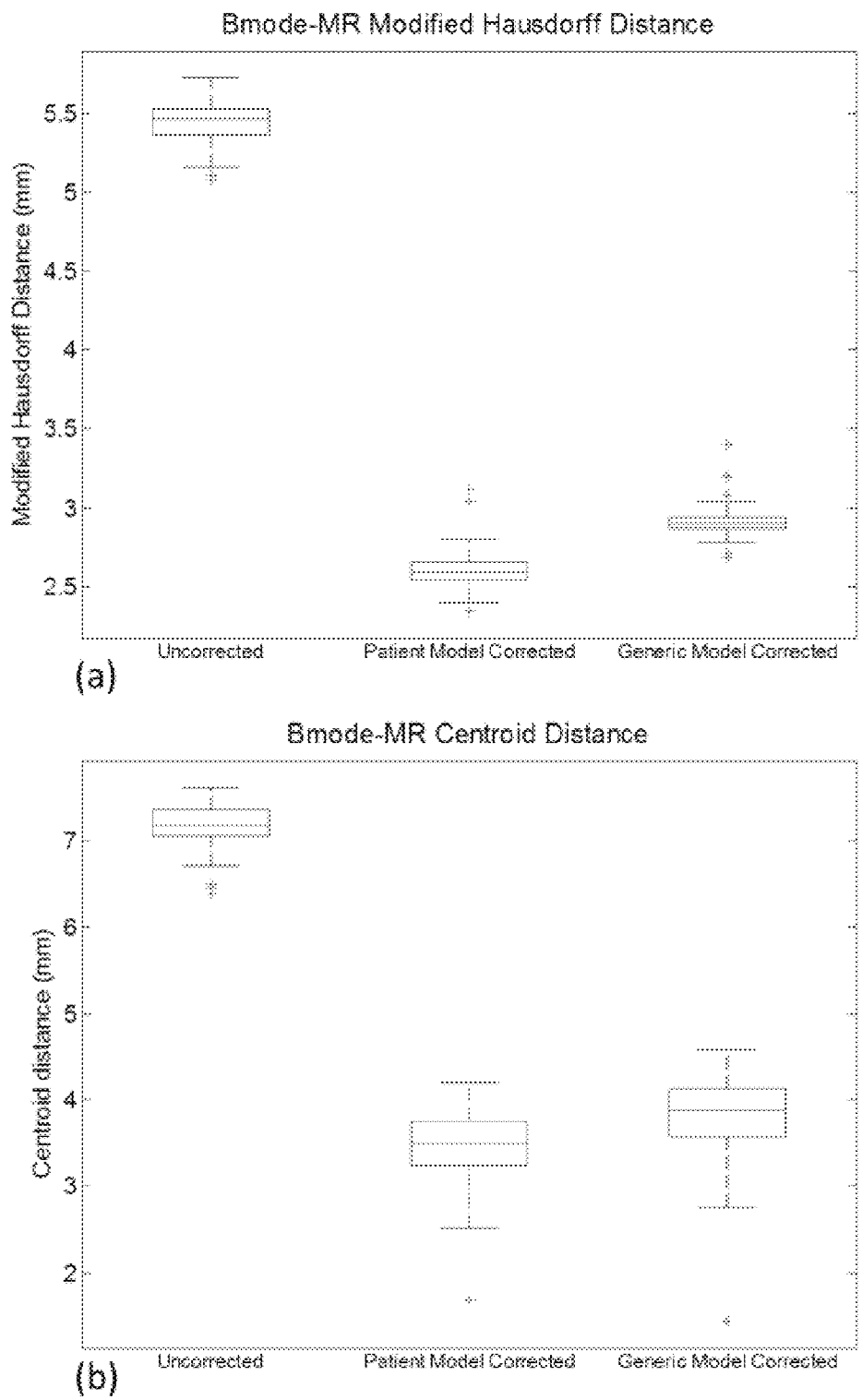
FIG. 12 shows alignment error results for the clinical case (n=118 B-mode images). The position of tumor borders was evaluated in terms of Modified Hausdorff Distance to the co-aligned MR borders (a), as well as the distance between the centroid of the ultrasound tumor with the co-planar MR tumor border (b). The edges of the boxes are the 25th and 75th percentiles, and the whiskers extend to the most extreme data points not considered as outliers.

The patient-specific and generic model corrections were deployed in the clinical case, and an exemplary result is shown in FIG. 11. The quantitative results of the clinical case in FIG. 12 show the MHD and co-planar-centroid distances as error metrics in comparing the ultrasound tumor borders with the co-registered CT borders, for both B-mode and strain images. The B-mode MHD values for the uncorrected, patient-specific corrected, and generic corrected tumor borders were 5.4±0.1 mm, 2.6±0.1 mm, and 2.9±0.1 mm, respectively. A Wilcoxon signed rank test was computed for the null hypothesis that the median difference between the error metrics was zero. It was found that there was a statistically significant difference between each of the image populations using this metric (p<0.01). The B-mode centroid error values for the uncorrected, patient-specific corrected, and generic corrected tumor borders were 7.2±0.2 mm, 3.5±0.4 mm, and 3.8±0.4 mm, respectively. The Wilcoxon test again found the three image populations to be significantly different from one another based on this metric (p<0.01).

Computational Efficiency

In order to provide an estimate of the computational speed offered by the generic correction framework, the time to compute the generic model solution for an image slice in the phantom B-mode dataset was recorded in the case of a 10×10×5 cm block mesh with 5 mm edge length including 4,042 nodes and 19,672 tetrahedral elements. When taking into account the condensation approach, the number of nodes and elements used in the generic correction was reduced to 697 and 2,698, respectively. The analogous correction using the patient-specific correction was computed using a mesh with 5 mm edge length including 10,989 nodes and 55,165 tetrahedral elements. The difference in the numbers of nodes and elements in the meshes having similar edge length corresponds to the difference between the volume of the full patient-specific organ versus the volume of the block of tissue in the generic method of the invention.

A breakdown of the various computational costs in terms of execution time for the patient-specific correction and generic correction is given in Table 1. In the case of the patient-specific method, the mesh is created from preoperative imaging, which typically requires at least 30 min assuming that some manual oversight of the image segmentation is required. Creation of the mesh from the segmentation mask takes at least 5 minutes. In terms of actual intraoperative expense, the construction of the 32967×32967 stiffness matrix K and the solution of equation (2) were conducted together in approximately 50 s, and this represented the vast majority of the total intraoperative computation time of 52.5 s.

In the case of the generic method, the modified stiffness matrix given by equation (6) was pre-computed for the block mesh prior to collection of ultrasound data. There were only 697 nodes in the ultrasound plane region of the mesh, and so the condensed stiffness matrix in this case contained 2091×2091 entries. For each model correction, the vector given by equation (7) was modified with the detected compression vectors and equation (5) was solved for the plane node displacements. The inverse of the modified stiffness matrix in equation (6) was stored and the solution time for the model was approximately 10 ms. The overall intraoperative computation time was approximately 80 ms.

TABLE 1

Approximate execution time for each step in the patient-specific and the generic correction methods, where the time was determined using a single thread of an Intel Core 2 Quad CPU at 2.4 GHz.

| | | Patient-Specific Correction | Generic Correction |
|---|---|---|---|
| Preoperative Phase | Image Segmentation | 30 min | — |
| | Mesh Construction | 5 min | 2 min |
| | Mesh Calibration | N/A | 2 min |
| | Stiffness Matrix Pre-construction | N/A | 1 min |
| | TOTAL | 35 min | 5 min |
| Intraoperative Phase | Boundary Condition Determination | 50 ms | 50 ms |
| | Stiffness Matrix Construction | 40 s | N/A |
| | Model Solve | 12 s | 10 ms |
| | Ultrasound Tumor Interpolation | 0.4 s | 20 ms |
| | TOTAL | 52.5 s | 80 ms |

DISCUSSION

Simulations

The first simulation study of the mesh resolution sensitivity shown in FIG. 6 shows that in all but the largest tumors, there is less than an approximate 5% difference between mesh solutions when the element edge length is approximately 5 mm. This would suggest that in domains with large heterogenities more care and finer resolution may be needed but as a routine method, 5 mm edge lengths may be sufficient.

The second simulation study showed how the block mesh size, tumor size, and tumor stiffness affect the model solution. The first observation is that the size of the block mesh did not affect the solution at the tumor nodes until the size was much larger than the depth at which the tumor was located (recall the tumor was placed at 3 cm to be in the center of a 6 cm US image). The solutions at the tumor nodes were similar when utilizing block sizes of 10×10×5 cm and 10×10×10 cm, but at the 10×10×15 cm size the tumor solutions tended to become less variable across different tumor sizes and stiffness. One trend to note from FIG. 7 is that there is very little impact on the model solution from the size of a tumor or its stiffness ratio at low levels of surface compression. However, as the surface compression becomes quite large, there is a divergence in the solutions on the basis of both tumor size (illustrated by the displacement magnitudes in each graph) and the stiffness ratio (the vertical axis on each graph). Larger tumor size resulted in greater overall tumor boundary deformation, which was expected because a larger tumor diameter implies that a greater proportion of tumor nodes were closer to the surface deformation, since all three tumors were placed at the same tissue depth. It is especially worth observing that the importance of tumor stiffness increased with increasing tumor size. In the case of the 10 mm diameter tumor at the maximum surface displacement of 10 mm, the difference in mean tumor displacements when using the 1:1 and 30:1 stiffness ratios varied by approximately 1 mm. However, in the case of the 40 mm diameter tumor, the difference in mean tumor displacements when using the 1:1 and 30:1 stiffness ratios varied by approximately 3 mm for the same surface displacement magnitude. These simulations indicate that although in many cases the tumor geometry and material properties do not greatly impact the model solution, these variables can become important when the target is a large tumor with a much different stiffness from the surrounding normal tissue. This becomes somewhat of a limitation for the generic method as with the generic method the mesh is pre-computed based on a homogeneous domain. There may be some superposition and weighted combinatorial possibilities that could account for stiffness variations that would entail more pre-computation but would likely reduce these errors. While this is outside the scope of this paper, it does provide some intriguing directions for the work.

The third simulation showed the effect of tumor location within the organ on the correction. The main observation from FIG. 8 is the trend in tumor boundary error reduction after application of the generic correction compared to the uncorrected error. These simulations predict very well the subsequent results observed in the phantom and clinical experiments. It is also interesting to note the consistent behavior of the correction regardless of the tumor location and the local organ geometry. For instance, the median boundary error for the tumor in Location 1 was reduced from a median value of 6.3 mm to 1.7 mm, over a 70% reduction. In the case of the tumor in Location 3, which was located deep in a thick region of the organ and thus was not deformed as much, the median uncorrected error was only 1.8 mm and was still reduced to 0.8 mm, over a 50% reduction. This finding is significant because it demonstrates that even with varying deformation scenarios due to tumor location, the generic correction method can improve tumor localization accuracy compared to no correction.

Phantom Experiments

The results of the compression correction methods shown in FIG. 10 clearly demonstrate the improvement offered by both the patient-specific and generic methods to the alignment between ultrasound and co-registered tomograms in the phantom experiments. The MHD error metric showed a significant decrease in misalignment after application of both methods, but with a greater decrease for the patient-specific method. The centroid distance error metric showed an even clearer improvement after applying the two model-based corrections compared to the uncorrected ultrasound images. Interestingly, a similar trend was noted with respect to the corrections, in that the patient-specific method resulted in a greater decrease in error overall compared to the generic model correction. However, although the correction for the patient-specific method was considered significantly better than the generic method according to the Wilcoxon test, the mean difference between the resultant errors for these correction frameworks was submillimetric for both the B-mode and strain images. This result is important because it indicates that the generic model correction performs nearly as well as the patient-specific method, making it a reasonable alternative for cases in which a patient-specific model may not be available or is too cumbersome computationally.

Clinical Case

The results of the clinical case in FIG. 12 showed a clear improvement in alignment between the tracked B-mode and MR tumor borders after both of the correction methods. The same trend from the phantom dataset was noted in this case, which was that the patient-specific model correction yielded a slightly greater reduction in error than the generic model correction. However, as with the phantom data, the difference in the mean error for both metrics was submillimetric in comparing the two corrections. This reinforces the idea that the generic model correction could be used to perform a comparable compression correction in the absence of a patient-specific model from preoperative imaging or when computational speed is paramount.

Computational Efficiency

It was found that the patient-specific method on average needed approximately 50 s to provide a compression correction update to each individual ultrasound frame during freehand movement of the probe. This long computation time was primarily a consequence of the need to reassign boundary condition types to surface nodes in the patient-specific mesh as the probe was moved around the tissue, thus necessitating a full reconstruction of the stiffness matrix K for each correction. The stiffness matrix for the patient-specific mesh was much larger than the mesh in the generic correction due to the greater number of nodes needed to represent the full patient organ, thus leading to a longer solution time as well. It should be noted that with some clever storage strategies, the potential to nearly eliminate the 40 s element assembly construction is likely, but one would still be faced with an approximate 12.5 s process. Regardless, these correction timesstill remove one of the primary advantages of ultrasound as an interventional imaging modality, which is its real-time data acquisition. There is clearly motivation to provide both a corrected image while maintaining a high frame rate.

By contrast, the generic correction method was shown to provide a model solution in approximately 10 ms using the condensation method to only solve for the mesh nodes in the immediate vicinity of the ultrasound plane. This essentially represents the removal of the primary computational bottleneck from the patient-specific correction, which was the 52.5/12.5 s required for construction and solution of the stiffness matrix for a large organ-shaped mesh. The rest of the intraoperative steps included determining boundary conditions prior to the model solution and then interpolating the model solution to the ultrasound data. The other steps combine with the model solution to give a total intraoperative correction time of approximately 80 ms, which is nearly real-time at 12.5 frames per second. In addition, this work was implemented on only a single CPU, and could easily be further improved by the use of GPU programming. In closing, thr exemplary study demonstrates that although there is a modest reduction of the accuracy of the solution provided by the generic correction versus the patient-specific method that is statistically significant, the dramatic computational benefit provided by the former at a cost of minor inaccuracy cannot be discounted.

Limitations

The generic model correction of the invention shares many of the same limitations of the patient-specific correction enumerated in [5]. For example, the generic correction is still subject to several sources of propagating error in the image guidance workflow. It heavily relies upon the optical tracking system, which imparts an inherent error to each measurement made with the device, including the surface digitization using a tracked pointer or LRS, as well as the tracked ultrasound data. It also retains the assumption from the patient-specific method that the user applies the probe purely in the depth direction for each image acquisition. This again simplified the creation of boundary conditions for the model, which is a challenge shared by both methods. In addition to the accuracy of the boundary conditions, the geometry of the mesh itself was likely the primary cause for the difference in error observed between the generic model correction and the patient-specific correction. A block of tissue is clearly a very simplistic representation of most anatomical structures on which this method would be used. The size of the block mesh also needs to be chosen before the correction can occur. Although a 10×10×10 cm cube was used for each generic model correction for the phantoms and clinical case in this study, it would be possible to pre-construct block meshes of various sizes as shown in FIG. 4 based on observable knowledge of the anatomy of interest that could be selected during the procedure. It would be fairly trivial to exchange various pre-constructed block meshes of different depths intraoperatively. The most computationally expensive operation during the procedure would be computing the compression depth using the LRS or pointer point cloud, and then performing the interpolation of the solution to the ultrasound data. It would conceivably be possible to perform these all of the operations in Table 1 at a real-time frame rate if efficiently implemented and with the support of GPU programming. Going a bit further, it might be possible to pre-compute the full displacement field on the slide itself, although this raises questions as to how to handle applications of the probe in compression that are not uniform. More than likely, a lookup table with an interpolation and superposition scheme could be used intraoperatively to select the solution combination corresponding to the correct compression magnitude. This would likely result in an additional speedup compared to the current results although validation of this approach would be needed.

Another assumption retained in the generic correction method was the assignment of material properties to the finite element mesh. Accurate intraoperative measurement of tissue mechanical properties is very challenging in practice. The approach taken in this work was to assume the mesh was composed of a single homogenous tissue type. Under this assumption, the biomechanical model solution would become less accurate with increasing contrast in tissue stiffness. It should be noted that only the relative stiffness values would affect the solution of the model in either the patient-specific or the generic model correction because only Dirichlet boundary conditions drive the solution. Absolute values for Young's modulus would only affect the solution if force conditions were integrated into the approach. Similar to the previous discussions regarding pre-computing the displacement field itself, it is likely that a pre-computational strategy that uses superposition and combinatorial approaches intraoperatively could be used to account for stiffness differences driven by perhaps strain-imaging data which is an intriguing direction for future improvements.

Although it is true that the assumptions and simplifications made in the exemplary embodiments could be seen as defeating the purpose of a patient-specific biomechanical model, these simplifications can be interpreted as methodologies that allow for improved fidelity measurements within the context of soft-tissue image guided environments. More specifically, when one considers the amount of tissue deformation that is experienced during the presentation of open or laparoscopic liver resection as an example, the generic framework allows for some re-establishment of measurement fidelity of subsurface structures acquired by ultrasound imaging. Ultimately, as guidance systems continue towards the full employment of nonrigid approaches for registration, the need for accurate localization of tissue structure within a consistent patient space that is workflow sensitive will be of high importance. This balance of accuracy and workflow within the context of sparse data will remain of paramount concern in these new paradigms.

A final limitation of both the patient-specific and generic methods is that each requires a surface acquisition during the procedure, which in the setup was provided by LRS. It is generally understood that adding hardware requirements to a procedure would limit its adoption. However, there are four aspects to this to consider. The first is that in certain procedures with very high accuracy requirements, such as neurosurgery, the added benefits of an enhanced spatial understanding of the interventional target may justify the hardware burden. The second aspect is that there are other methods besides an LRS device which can be used to provide the necessary surface measurement. For example, some have proposed to use a tracked ultrasound probe itself as a surface digitizer by swabbing the surface [18], and others have proposed to use stereoscopic surgical cameras to construct the organ surface [19]. A third consideration is that standardized surface acquisition is likely on the horizon for image guided surgery systems. For example, surface registration via swabbing is already a standard feature on many commercial image guided platforms. The last point is it is possible to trigger this correction using contact-conditions by monitoring the ultrasound imaging data itself as it comes into contact with the tissue. This has its own challenges but is certainly worth considering. Nevertheless, much of the equipment utilized in this work is already routinely available in many operating rooms or can be modified to acquire appropriate data (e.g., stereo-pair is a standard feature in surgical microscopes). The method used for digitizing the surface is just one embodiment of a more general concept.

The overall result of this work is that information in tracked ultrasound data can be corrected in near real-time, provided that a measure of tissue compression is available intraoperatively. The immediate benefits are obvious in providing the clinician with more accurate size and position measurements of subsurface targets. This is important in a wide variety of procedures and anatomy, such as determining resection or ablation margins. Additionally, there are implications for more speculative work using subsurface information for enhanced registration [20]. An analysis of the effects of integrating corrected and uncorrected ultrasound data in a registration framework would be very interesting.

To inventors' knowledge there are no similar commercial products that are capable of doing this. In the academic literature, competitive approaches include using image intensity-based registration of compressed ultrasound images to an uncompressed ultrasound image to perform the compression correction. The approach avoids the challenging task of ultrasound image registrations, which is highly reliant on the image profile which can be quite variable. Another competitive approach in the literature is to mount a force transducer to the tip of the ultrasound probe to measure the pressure exerted by the probe on the soft tissue, and to use this pressure as part of a model of the tissue. However, the invented method uses surface displacements to drive the model instead of force, and avoids the use of a force transducer.

In sum, the invention recites, among other things, a novel method for correcting tissue compression error exerted by an ultrasound probe. In certain embodiments, the method uses a biomechanical model to predict how the soft tissue is being manipulated during ultrasound imaging, and uses this model prediction to correct the ultrasound data from a compressed to an uncompressed state. Specifically, the generic tissue model was used to estimate physical tissue deformation as a result of pressing the tracked probe into the tissue surface and also compared to a previous compensation framework as well as to gold standard intraoperative CT imaging measurements. The experimental results indicate that the generic model correction method provides significantly improved intraoperative localization data. This is particularly important when patient-specific models may not be available from preoperative imaging or when minimizing computational encumbrance is important. In addition, the techniques developed are such that real-time compensation is possible. There is currently no system on the market that is capable of aligning soft-tissue-compressed compromised ultrasound images in real time. Moreover, the method overcomes the problem of accurate alignment of ultrasound images (which are often distorted due to pressing the ultrasound probe into soft tissue) with other data available intraoperative which do not contain these compression effects. It serves as a fundamental breakthrough towards correlating intraoperative ultrasound images to other intraoperative/preoperative imaging modalities.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

LIST OF REFERENCES

[1]. Treece G M, Gee A H, Prager R W (2005) RF and amplitude-based probe pressure correction for 3D ultrasound. Ultrasound Med Biol 31 (4):493-503. doi:S0301-5629(04)00441-7 [pii] 10.1016/j.ultrasmed-bio.2004.12.018.

[2]. Xiao G, Brady J M, Noble J A, Burcher M, English R (2002) Nonrigid registration of 3-D free-hand ultrasound images of the breast. IEEE Trans Med Imaging 21 (4): 405-412. doi:10.1109/TMI.2002.1000264.

[3]. Burcher M R, Lianghao H, Noble J A Deformation correction in ultrasound images using contact force measurements. In: Mathematical Methods in Biomedical Image Analysis, 2001. MMBIA 2001. IEEE Workshop on, 2001 2001. pp 63-70. doi:10.1109/mmbia.2001.991700.

[4]. Sun S-Y (2010) Deformation correction in ultrasound imaging in an elastography framework. Thesis S. M.—Massachusetts Institute of Technology Dept. of Electrical Engineering and Computer Science 2010, Massachusetts Institute of Technology, Cambridge.

[5]. Pheiffer T S, Thompson R C, Rucker D C, Simpson A L, Miga M I (2014) Model-Based Correction of Tissue Compression for Tracked Ultrasound in Soft Tissue Image-Guided Surgery. Ultrasound Med Biol. doi:S0301-5629(13)01146-0 [pii] 10.1016/j.ultrasmed-bio.2013.11.003.

[6]. Rucker D C, Wu Y, Clements L W, Ondrake J E, Pheiffer T S, Simpson A L, Jarnagin W R, Miga M I (2013) A Mechanics-Based Nonrigid Registration Method for Liver Surgery Using Sparse Intraoperative Data. Medical Imaging, IEEE Transactions on 33 (1):147-158. doi: 10.1109/tmi.2013.2283016

[7]. Lange T, Papenberg N, Heldmann S, Modersitzki J, Fischer B, Lamecker H, Schlag P M (2009) 3D ultrasound-CT registration of the liver using combined landmark-intensity information. International Journal of Computer Assisted Radiology and Surgery 4 (1):79-88. doi: DOI 10.1007/s11548-008-0270-1.

[8]. Chen I, Ong R E, Simpson A L, Sun K, Thompson R C, Miga M I (2013) Integrating Retraction Modeling Into an Atlas-Based Framework for Brain Shift Prediction. Ieee Transactions on Biomedical Engineering 60 (12):3494-3504. doi:Doi 10.1109/Tbme.2013.2272658.

[9]. Coffey A M, Miga M I, Chen I, Thompson R C (2013) Toward a preoperative planning tool for brain tumor resection therapies. International Journal of Computer Assisted Radiology and Surgery 8 (1):87-97. doi:DOI 10.1007/s11548-012-0693-6.

[10]. Bro-Nielsen M (1998) Finite element modeling in surgery simulation. Proceedings of the IEEE 86 (3):490-503. doi:Doi 10.1109/5.662874.

[11]. Sullivan J M, Charron G, Paulsen K D (1997) A three-dimensional mesh generator for arbitrary multiple material domains. Finite Elements in Analysis and Design 25 (3-4):219-241. doi:Doi 10.1016/50168-874x(96) 00027-3.

[12]. Arun K S, Huang T S, Blostein S D (1987) Least-Squares Fitting of 2 3-D Point Sets. Ieee Transactions on Pattern Analysis and Machine Intelligence 9 (5):699-700.

[13]. Besl P J, Mckay N D (1992) A Method for Registration of 3-D Shapes. Ieee Transactions on Pattern Analysis and Machine Intelligence 14 (2):239-256.

[14]. Muratore D M, Galloway R L (2001) Beam calibration without a phantom for creating a 3-D freehand ultrasound system. Ultrasound in Medicine and Biology 27 (11): 1557-1566.

[15]. Pheiffer T S, Simpson A L, Lennon B, Thompson R C, Miga M I (2012) Design and evaluation of an optically-tracked single-CCD laser range scanner. Med Phys 39 (2):636-642. doi:10.1118/1.3675397.

[16]. Dubuisson M P, Jain A K A modified Hausdorff distance for object matching. In: Pattern Recognition,

[17]. Dumpuri P, Thompson R C, Dawant B M, Cao A, Miga M I (2007) An atlas-based method to compensate for brain shift: preliminary results. Med Image Anal 11 (2):128-145. doi:51361-8415(06)00081-8 [pii] 10.1016/j.media.2006.11.002.

[18]. Miller K E, Ondrake J E, Pheiffer T S, Simpson A L, Miga M I Utilizing ultrasound as a surface digitization tool in image guided liver surgery. In: David R H, III, Kenneth H W (eds), 2012. SPIE, p 83163D.

[19]. Kumar A N, Miga M I, Pheiffer T S, Chambless L B, Thompson R C, Dawant B M (2015) Persistent and automatic intraoperative 3D digitization of surfaces under dynamic magnifications of an operating microscope. Medical Image Analysis 19 (1):30-45. doi:DOI 10.1016/j.media.2014.07.004.

[20]. Lange T, Eulenstein S, Hunerbein M, Lamecker H, Schlag P M (2004) Augmenting intraoperative 3D ultrasound with preoperative models for navigation in liver surgery. Medical Image Computing and Computer-Assisted Intervention—Miccai 2004, Pt 2, Proceedings 3217:534-541.

What is claimed is:

1. A method for real-time correction of tissue compression for tracked ultrasound, comprising:
   acquiring an ultrasound image of tissues of interest with an ultrasound probe having a probe surface, wherein the ultrasound probe is tracked to provide a position and an orientation of the probe surface of the ultrasound probe for the acquired ultrasound image;
   acquiring intraoperative measurements of the undeformed tissue surface;
   constructing a generic grid representation of tissues for use with a mathematical model of tissue biomechanics, wherein the generic grid representation is pre-aligned to the acquired ultrasound image by performing a calibration to the ultrasound probe;
   determining boundary conditions to the mathematical model of tissue biomechanics represented by the generic grid representation;
   solving the mathematical model of tissue biomechanics for three-dimensional (3D) displacements in the generic grid representation of the tissues; and
   performing correction of tissue compression by using the reversed and interpolated 3D displacement field on the acquired ultrasound image,
   wherein the step of acquiring the ultrasound image further comprises calibrating the ultrasound image to a tracked target that is attached to the ultrasound probe, wherein the ultrasound probe is tracked intraoperatively with a tracking device, so that the pose of the ultrasound image is defined in the coordinate system of the tracking device;
   wherein the step of acquiring the intraoperative measurements of the undeformed tissue surface is performed with a surface acquiring device that is tracked intraoperatively with the tracking device or contains a geometric reference within the field of view of the surface acquiring device; and
   wherein the step of determining the boundary conditions comprises using the undeformed tissue surface in conjunction with the position and orientation of the ultrasound probe to estimate a depth to which the tissues are compressed, wherein the depth is computed by casting rays down from each point of the cloud obtained by the surface acquiring device in the depth direction, and finding an average length of the ray segments which intersect with the probe surface.

2. The method of claim 1, wherein the pose of the generic grid representation is defined by the same tracking information which defines the pose of the ultrasound image, wherein the tracking information is an optically tracked attached target or electromagnetically attached tracked target.

3. The method of claim 1, wherein the surface acquiring device is used to construct a digital representation of the probe surface.

4. The method of claim 1, wherein the surface acquiring device comprises a laser range scanner (LRS) or a stereo pair camera set.

5. The method of claim 1, wherein the depth is used to assign Dirichlet boundary conditions to the mathematical model on the generic grid representation.

6. The method of claim 1, wherein the boundary conditions for the mathematical model associated with the generic grid representation are assigned such that the far-field face of the generic grid representation is fixed, and the superior and side surfaces are stress-free.

7. The method of claim 1, wherein the mathematical model associated with the generic grid representation calibration is performed by aligning the top of the ultrasound image with the center of one side of the generic grid representation, and aligning the image plane itself with the plane through the center of the generic grid representation.

8. The method of claim 1, further comprising registering the surface information to preoperative imaging for determining the boundary conditions.

9. The method of claim 1, wherein the generic grid representation of tissues is constructed from preoperative imaging and registered to intraoperative space.

10. A method for real-time correction of tissue compression for tracked ultrasound, comprising:
    acquiring an ultrasound image of tissues of interest with an ultrasound probe having a probe surface, wherein the ultrasound probe is tracked to provide a position and an orientation of the probe surface of the ultrasound probe for the acquired ultrasound image;
    acquiring intraoperative measurements of the undeformed tissue surface;
    constructing a generic grid representation of tissues for use with a mathematical model of tissue biomechanics, wherein the generic grid representation is pre-aligned to the acquired ultrasound image by performing a calibration to the ultrasound probe;
    determining boundary conditions to the mathematical model of tissue biomechanics represented by the generic grid representation;
    solving the mathematical model of tissue biomechanics for three-dimensional (3D) displacements in the generic grid representation of the tissues; and
    performing correction of tissue compression by using the reversed and interpolated 3D displacement field on the acquired ultrasound image,
    wherein the step of determining the boundary conditions comprises using the location of the ultrasound probe as defined by tissue contact determined by detection within the ultrasound image in conjunction with the final position and orientation of the ultrasound probe at the time of subsurface tissue structure visualization to estimate a depth to which the tissues are compressed, wherein the depth is computed by estimating compression depth as determined by analyzing the difference in the probe location between the initial tissue contact and the final structure visualization.

11. The method of claim 10, wherein the depth is used to assign Dirichlet boundary conditions to the mathematical model on the generic grid representation.

12. A method for real-time correction of tissue compression for tracked ultrasound, comprising:
acquiring an ultrasound image of tissues of interest with an ultrasound probe having a probe surface, wherein the ultrasound probe is tracked to provide a position and an orientation of the probe surface of the ultrasound probe for the acquired ultrasound image;
acquiring intraoperative measurements of the undeformed tissue surface;
constructing a generic grid representation of tissues for use with a mathematical model of tissue biomechanics, wherein the generic grid representation is pre-aligned to the acquired ultrasound image by performing a calibration to the ultrasound probe;
determining boundary conditions to the mathematical model of tissue biomechanics represented by the generic grid representation;
solving the mathematical model of tissue biomechanics for three-dimensional (3D) displacements in the generic grid representation of the tissues; and
performing correction of tissue compression by using the reversed and interpolated 3D displacement field on the acquired ultrasound image,
wherein the mathematical model is governed by a standard 3D Navier-Cauchy equation for the 3D displacements;
wherein the generic grid representation is represented by a mesh comprising nodes in the form of a generic block;
wherein the displacement vector at each node in the block mesh satisfy with:

$$[K]\{u\}=\{f\}$$

where K is the global stiffness matrix, u is the vector of nodal displacements, and f contains the contributions of boundary conditions; and
wherein the boundary conditions assigned to each boundary node remains the same, such that a stiffness matrix K is pre-computable and reusable for each correction, wherein a vector of nodal displacements u satisfies with:

$$\{u\}=[K]^{-1}\{f\}$$

where f contains contributions of the boundary conditions.

13. The method of claim 12, further comprising arranging the order of the mesh node indices to ensure that first N equations belong to the nodes lying on the ultrasound plane, and any nodes on the top surface which are assigned varying amounts of compression boundary conditions, wherein the equation of the displacement vector is expressed as a block matrix system where the subscripts p and a indicate the plane nodes and all other nodes, respectively:

$$\begin{bmatrix} K_{pp} & K_{pa} \\ K_{ap} & K_{aa} \end{bmatrix} \begin{Bmatrix} u_p \\ u_a \end{Bmatrix} = \begin{Bmatrix} f_p \\ f_a \end{Bmatrix}.$$

14. The method of claim 13, wherein the block matrix system is rearranged to a form involving only the displacement solution of the plane nodes, $u_p$:

$$[\check{K}_{pp}]\{u_p\}=\{\check{f}_s\}$$

where $$[\check{K}_{pp}]=[K_{aa}]-[K_{pa}][K_{aa}]^{-1}[K_{ap}]$$

$$\{\check{f}_s\}=\{f_s\}-[K_{pa}][K_{aa}]^{-1}\{f_a\}$$

wherein the modified stiffness matrix $[\check{K}_{pp}]$ represents a transfer of the displacements from all non-plane nodes to the plane nodes, and maintains the volumetric nature of the model, wherein the modified stiffness matrix $[\check{K}_{pp}]$ is a fraction of the size of the full K matrix, and wherein the $u_p$ vector of plane node displacements is pre-computed and stored in a lookup table.

15. The method of claim 14, wherein all nodes in the $f_a$ vector is assigned either zero stress or zero displacement boundary conditions, wherein changes in the compression depth during ultrasound imaging results in a reassignment of the values in $\check{f}_s$:

$$\{\check{f}_s\}\big|_{\{f_a\}=0}=\{f_s\}.$$

16. The method of claim 13, wherein subsets designated with respect to planes represent a subvolume within an ultrasound imaging volume used with multi-dimensional ultrasound arrays.

17. A system for real-time correction of tissue compression for tracked ultrasound, comprising:
an ultrasound probe configured to acquire an ultrasound image of tissues of interest;
a surface acquiring device configured to perform intraoperative measurements of the undeformed tissue surface;
a tracking device configured to track the ultrasound probe and the surface acquiring device; and
a controller coupled with the ultrasound probe, the surface acquiring device and the tracking device and configured to construct a generic grid representation of tissues for use with a mathematical model of tissue biomechanics, wherein the generic grid representation is pre-aligned to the acquired ultrasound image by performing a calibration to the ultrasound probe; solve the mathematical model of tissue biomechanics for three-dimensional (3D) displacements in the generic grid representation of the tissues, and perform the correction of tissue compression by using the reversed and interpolated 3D displacement field onto the acquired ultrasound image,
wherein the ultrasound probe is tracked by the tracking device with a tracked attached target to provide a position and an orientation of the probe surface of the ultrasound probe for the acquired ultrasound image;
wherein the controller is further configured to calibrate the ultrasound image to the tracked attached target, so that the pose of the ultrasound image is defined in the coordinate system of the tracking device; and
wherein the controller is further configured to determine boundary conditions using the undeformed tissue surface in conjunction with the position and orientation of the ultrasound probe to estimate a depth to which the tissues are compressed, wherein the depth is computed by casting rays down from each point of the cloud obtained by the surface acquiring device in the depth direction, and finding an average length of the ray segments which intersect with the probe surface.

18. The system of claim 17, wherein the surface acquiring device is further configured to construct a digital representation of the probe surface.

19. The method of claim 17, wherein the surface acquiring device comprises a laser range scanner (LRS) or a stereo pair camera set.

20. The system of claim 17, further comprising a display for displaying at least the ultrasound image, the generic grid representation of the tissues, and the correction of tissue compression.

21. A system for real-time correction of tissue compression for tracked ultrasound, comprising:
an ultrasound probe configured to acquire an ultrasound image of tissues of interest;
a surface acquiring device configured to perform intraoperative measurements of the undeformed tissue surface;
a tracking device configured to track the ultrasound probe and the surface acquiring device; and
a controller coupled with the ultrasound probe, the surface acquiring device and the tracking device and configured to construct a generic grid representation of tissues for use with a mathematical model of tissue biomechanics, wherein the generic grid representation is pre-aligned to the acquired ultrasound image by performing a calibration to the ultrasound probe; solve the mathematical model of tissue biomechanics for three-dimensional (3D) displacements in the generic grid representation of the tissues, and perform the correction of tissue compression by using the reversed and interpolated 3D displacement field onto the acquired ultrasound image,
wherein the controller is further configured to determine boundary conditions using the undeformed tissue surface as determined by recording the orientation and position of the ultrasound probe at first contact with the tissue in the ultrasound image in conjunction with the position and orientation of the ultrasound probe when placed to visualize the subsurface target, wherein the difference in these positions is used to estimate a depth to which the tissues are compressed.

22. A non-transitory computer-readable medium storing instructions which, when executed by one or more processors, cause a controller to perform functions for real-time correction of tissue compression for tracked ultrasound, the functions comprising:
calibrating an ultrasound image acquired with an ultrasound probe to a tracked target attached to the ultrasound probe;
acquiring intraoperative measurements of the undeformed tissue surface;
constructing a generic grid representation of tissues for use with a mathematical model of tissue biomechanics, wherein the grid representation is pre-aligned to the acquired ultrasound image by performing a calibration to the ultrasound probe;
determining boundary conditions to the mathematical model of tissue biomechanics represented by the generic grid representation;
solving the mathematical model of tissue biomechanics for three-dimensional (3D) displacements in the generic grid representation of the tissues; and
performing the correction of tissue compression by using the reversed and interpolated 3D displacement field onto the acquired ultrasound image,
wherein the function of determining the boundary conditions comprises the function of using the undeformed tissue surface in conjunction with the position and orientation of the ultrasound probe to estimate a depth to which the tissues are compressed, wherein the depth is computed by casting rays down from each point of the cloud obtained by a surface acquiring device in the depth direction, and finding an average length of the ray segments which intersect with the probe surface.

23. The non-transitory computer-readable medium of claim 22, wherein the pose of the ultrasound image is defined in the coordinate system of a tracking device.

24. The non-transitory computer-readable medium of claim 23, wherein the pose of the generic grid representation is defined by the same tracking information which defines the pose of the ultrasound image, wherein the tracking information is an optically tracked attached target or electromagnetically attached tracked target.

25. The non-transitory computer-readable medium of claim 22, wherein the functions further comprise constructing a digital representation of the probe surface.

26. The non-transitory computer-readable medium of claim 22, wherein the depth is used to assign Dirichlet boundary conditions to the mathematical model on the generic grid representation.

27. The non-transitory computer-readable medium of claim 22, wherein the boundary conditions for the mathematical model associated with the generic grid representation are assigned such that the far-field face of the generic grid representation is fixed, and the superior and side surfaces are stress-free.

28. The non-transitory computer-readable medium of claim 22, wherein the biomechanical model is governed by a standard 3D Navier-Cauchy equation for the 3D displacements.

29. A non-transitory computer-readable medium storing instructions which, when executed by one or more processors, cause a controller to perform functions for real-time correction of tissue compression for tracked ultrasound, the functions comprising:
calibrating an ultrasound image acquired with an ultrasound probe to a tracked target attached to the ultrasound probe;
acquiring intraoperative measurements of the undeformed tissue surface;
constructing a generic grid representation of tissues for use with a mathematical model of tissue biomechanics, wherein the grid representation is pre-aligned to the acquired ultrasound image by performing a calibration to the ultrasound probe;
determining boundary conditions to the mathematical model of tissue biomechanics represented by the generic grid representation;
solving the mathematical model of tissue biomechanics for three-dimensional (3D) displacements in the generic grid representation of the tissues; and
performing the correction of tissue compression by using the reversed and interpolated 3D displacement field onto the acquired ultrasound image,
wherein the function of determining boundary conditions comprises using the undeformed tissue surface as determined by recording the orientation and position of the ultrasound probe at first contact with the tissue in the ultrasound image in conjunction with the position and orientation of the ultrasound probe when placed to visualize the subsurface target, wherein the difference in these positions is used to estimate a depth to which the tissues are compressed.

* * * * *